United States Patent
Navarrete Solano et al.

(10) Patent No.: US 10,470,798 B1
(45) Date of Patent: Nov. 12, 2019

(54) METHODS FOR PROMOTING FERTILIZATION

(71) Applicant: Ohana Biosciences, Inc., Cambridge, MA (US)

(72) Inventors: Felipe A. Navarrete Solano, Medford, MA (US); Eric Steven Furfine, Lincoln, MA (US); Kathleen Inez Seyb, Wakefield, MA (US)

(73) Assignee: OHANA BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 16/282,217

(22) Filed: Feb. 21, 2019

Related U.S. Application Data

(60) Provisional application No. 62/773,471, filed on Nov. 30, 2018.

(51) Int. Cl.
- *A61B 17/43* (2006.01)
- *C12N 5/076* (2010.01)
- *C12N 5/073* (2010.01)

(52) U.S. Cl.
CPC .............. *A61B 17/43* (2013.01); *C12N 5/061* (2013.01); *C12N 5/0604* (2013.01); *C12N 2500/30* (2013.01); *C12N 2500/34* (2013.01)

(58) Field of Classification Search
CPC .. C12N 2517/10; C12N 5/0604; C12N 5/061; A61B 17/43; A61B 17/435; A61D 19/02; A61D 19/04
See application file for complete search history.

(56) References Cited

U.S. PATENT DOCUMENTS

| | | |
|---|---|---|
| 4,315,908 A | 2/1982 | Zer et al. |
| 5,135,759 A | 8/1992 | Johnson |
| 5,250,417 A | 10/1993 | Feuchter et al. |
| 5,474,890 A | 12/1995 | Di Virgilio et al. |
| 5,834,225 A | 11/1998 | Chou et al. |
| 6,309,815 B1 | 10/2001 | Tash et al. |
| 6,596,310 B1 | 7/2003 | Chou et al. |
| 7,838,210 B2 | 11/2010 | Ludwig et al. |
| 8,163,508 B2 | 4/2012 | O'Connor et al. |

(Continued)

FOREIGN PATENT DOCUMENTS

| | | |
|---|---|---|
| CN | 105154392 A | 12/2015 |
| CN | 106190955 A | 12/2016 |

(Continued)

OTHER PUBLICATIONS

Amaral, Alexandra et al., Exogenous glucose improves long-standing human sperm motility, viability, and mitochondrial function, Fertility and Sterility, vol. 96, No. 4, Oct. 2011, doi:10.1016/j.fertnstert.2011.07.1091.

(Continued)

*Primary Examiner* — Christine H Matthews
(74) *Attorney, Agent, or Firm* — Wilson, Sonsini, Goodrich & Rosati

(57) ABSTRACT

The disclosure provides, inter alia, methods of improving sperm function and related methods of fertilization, together with preparations of activated or potentiated sperm. The disclosure additionally provides articles of manufacture suitable for performing the methods provided by the invention. The methods provided by the disclosure, in some embodiments entail energy depletion with subsequent staged reintroduction of different energy sources.

20 Claims, 6 Drawing Sheets

(56) References Cited

U.S. PATENT DOCUMENTS

| | | | |
|---|---|---|---|
| 9,221,873 | B1 | 12/2015 | Chiu et al. |
| 2005/0003472 | A1 | 1/2005 | Anzar |
| 2012/0197068 | A1 | 8/2012 | Shimada et al. |

FOREIGN PATENT DOCUMENTS

| | | |
|---|---|---|
| WO | WO-9501799 A1 | 1/1995 |
| WO | WO-0107021 A2 | 2/2001 |
| WO | WO-2010005260 A2 | 1/2010 |
| WO | WO-2010104882 A1 | 9/2010 |
| WO | WO-2011108946 A1 | 9/2011 |
| WO | WO-2012061578 A2 | 5/2012 |
| WO | WO-2016135284 A1 | 9/2016 |
| WO | WO-2017159737 A1 | 9/2017 |
| WO | WO-2017173391 A1 | 10/2017 |

OTHER PUBLICATIONS

Aparicio, I.M. et al., Autophagy-related proteins are functionally active in human spermatozoa and may be involved in the regulation of cell survival and motility, Scientific Reports, pp. 1-19,:33647|DOI:10. 1038/5rep33647.

Baker, H. W., The human acrosome reaction, Asian journal of andrology, (Sep. 2000) vol. 2, No. 3, pp. 172-178. Ref: 34 Journal code: 100942132. ISSN: 1008-682X. L-ISSN: 1008-682X.

Bucci, Diego et al., GLUTs and Mammalian Sperm Metabolism, J. of Andrology, vol. 32, No. 4, Jul./Aug. 2011, pp. 348-355.

Burkin, H. R., Zona pellucida protein binding ability of porcine sperm during epididymal maturation and the acrosome reaction, Developmental biology, (Jun. 1, 2000) vol. 222, No. 1, pp. 99-109. Journal code: 0372762. ISSN: 0012-1606. L-ISSN: 0012-1606. DOI http://dx.doi.org/10.1006/dbio.2000.9707.

Chantler E., Effect of cooling on the motility and function of human spermatozoa, Cryobiology, (Sep. 2000) vol. 41, No. 2, pp. 125-134. Journal code: 0006252. ISSN: 0011-2240. L-ISSN: 0011-2240. DOI http://dx.doi.org/10.1006/cryo.2000.2274.

Co-pending U.S. Appl. No. 16/282,204, filed Feb. 21, 2019.

Co-pending U.S. Appl. No. 16/282,224, filed Feb. 21, 2019.

DasGupta, S., et al., A possible role for Ca2+-ATPase in human sperm capacitation, J. Reproduction and Fertility (1994) 102, 107-116.

Ford, W.C.L., Glycolysis and sperm motility: Does a spoonful of sugar help the flagellum go round? Human Reproduction Update, vol. 12, No. 3, pp. 269-274, 2006, doi:10.1093/humupd/dmi053.

Fraser, Lynn R. et al., Expression of capacitation-dependent changes in chlortetracycline fluorescence patterns in mouse spermatozoa requires a suitable glycolysable substrate, J. Reprod. Fert. (1990) 88, 611-621.

Goodson, Summer G. et al., CASAnova: a multiclass support vector machine model for the classification of human sperm motility patterns, Biology of Reproduction, 2017, 97(5), 698-708: doi: 10.1093/biore/iox120 Research Article, Advance Access Publication Date: Oct. 4, 2017.

Goodson, Summer G. et al., Metabolic substrates Exhibit Differential Effects on Functional Parameters of Mouse Sperm Capacitation, Biology of Reproduction (2012) 87(3):75, 1-15, Published online before print Jul. 25, 2012, DOI 10.1095/biorepord.112. 102673.

Hereng, T.H., Exogenous pyruvate accelerates glycolysis and promotes capacitation in human spermatoza, Human Reproduction, vol. 26, No. 12, pp. 3249-3263, 2011.

Jung, Min et al., Unified single-cell analysis of testis gene regulation and pathology in 5 mouse strains, bioRxiv reprint first posted online Aug. 16, 2018: doi:http://dx.doi.org/10.1101/393769.

Klastrup, Line Katrine et al., The influence of paternal diet on sncRNA-mediated epigenetic inheritance, Molecular Genetics and Genomics, Sep. 18, 2018, https://doi.org/10.1007/s00438-018-1492-8.

Krapf, Dario, et al., Calcineurin Regulates Progressive Motility Activation of Rhinella (Bufo arenarum) Sperm Through Dephosphorylation of PKC Substrates, Journal of Cellular Physiology, (Oct. 2014) vol. 229, No. 10, pp. 1378-1386. http://onlinelibrary.wiley.com/journal/10.1002/(ISSN)1097-4652. CODEN: JCLLAX. ISSN: 0021-9541. E-ISSN: 1097-4652, DOI 10.1002/jcp.24571.

Leese, H.J., The formulation and function of oviduct fluid, J. Reprod. Fert. (1988) 82,843-856.

Lefievre, Linda, Activation of protein kinase a during human sperm capacitation and acrosome reaction. Journal of Andrology, (Sep.-Oct. 2002) vol. 23, No. 5, pp. 709-716. print.

Luis De La Vega-Beltran, Jose et al., Mouse Sperm Membrane Potential Hyperpolarization Is Necessary and Sufficient to Prepare Sperm for the Acrosome Reaction, Journal of Biological Chemistry, (Dec. 28, 2012) vol. 287, No. 53, pp. 44384-44393. http://www.jbc.org/. CODEN: JBCHA3. ISSN: 0021-9258. E-ISSN: 1083-351X. DOI 10.1074/jbc.M112.393488.

McPartlin, L. A. et al., Guanine-Nucleotide Exchange Factors (RAPGEF3/RAPGEF4) Induce Sperm Membrane Depolarization and Acrosomal Exocytosis in Capacitated Stallion Sperm., Biology of Reproduction, (Jul. 2011) vol. 85, No. 1, pp. 179-188. CODEN: BIREBV. ISSN: 0006-3363. E-ISSN: 1529-7268. DOI 10.1095/biolreprod.110.085555.

Miki, K., energy metabolism and sperm function, Soc Reprod Fertil Suppl. 2007: 65;309-25., www.ncbi.nlm.nih.gov/pubmed/?term=17644971&report=abstract&format=text.

Morbeck, Dean E. et al., Composition of commercial media used for human embryo culture, Sep. 2014;102(3): 759-766.e9. doi: 10.1016/j.fertnstert.2014.05.043. Epub Jul. 4, 2014.

Nascimento, Jaclyn, et al., Comparison of Glycolysis and Oxidative Phosphorylation as Energy Sources for Mammalian Sperm Motility, Using the Combination of Fluorescence Imaging, laser Tweezers, and Real-time automated Tracking and Trapping, J. Cellular Physiology, 217:745-751, 2008.

Navarrete, Felipe A. et al., Transient exposure to calcium ionophore enables in vitro fertilization in sterile mouse models, Scientific Reports, (Sep. 15, 2016) vol. 6, pp. Article No. 33589. http://www.nature.com/srep. ISSN: 2045-2322. E-ISSN: 2045-2322. 10.1038/srep33589.

Newton Larissa D., Na+/K+ATPase regulates sperm capacitation through a mechanism involving kinases and redistribution of its testis-specific isoform., Molecular reproduction and development, (Feb. 2010) vol. 77, No. 2, pp. 136-148. Journal code: 8903333. E-ISSN: 1098-2795. L-ISSN: 1040-452X. Report No. PMC-PMC5059152; MID-CAMS1894. DOI http://dx.doi.org/10.1002/mrd.21114 CY United States.

Oh, Y. S., Fucosyl neoglycoprotein binds to mouse epididymal spermatozoa and inhibits sperm binding to the egg zona pellucida. Andrologia, (Dec. 2013) vol. 45, No. 6, pp. 363-368. Electronic Publication Date: Sep. 23, 2012, Journal code: 0423506. E-ISSN: 1439-0272. L-ISSN: 03034569.DOI http://dx.doi.org/10.1111/and. 12024.

Parrish, J. J., Capacitation of bovine sperm by heparin: inhibitory effect of glucose and role of intracellular pH., Biology of reproduction, (Oct. 1989) vol. 41, No. 4, pp. 683-699. Journal code: 0207224. ISSN: 0006-3363. L-ISSN: 0006-3363.

Portela, J.M.D. et al., High glucose concentrations per se do not adversely affect human sperm function in vitro, 2015, Reproduction 2015) 150: 77-84, DOI: 10.1530/rep-15/0100.

Qin, Xuebin et al., Further characterization of reproductive abnormalities in mCd59b knock out mice: A potential new function of mCd59 in male reproduction, Journal of Immunology, (Nov. 15, 2005) vol. 175, No. 10, pp. 6294-6302. http://www.jimmunol.org.

Quinn P., Successful human in vitro fertilization using a modified human tubal fluid medium lacking glucose and phosphate ions. Fertility and sterility, (Apr. 1995) vol. 63, No. 4, pp. 922-924. Journal code: 0372772. ISSN: 0015-0282. L-ISSN: 0015-0282.

Quinn, Patrick, Enhanced Results in Mouse and Human Embryo Culture Using a Modified Human Tubal Fluid Medium Lacking Glucose and Phosphate, J. Assisted Reproduction and Genetics, vol. 12, No. 2, 1995, pp. 97-105.

Riel, Jonathan M. et al., Short-Term storage of human spermatozoa in electrolyte-free medium without freezing maintains sperm chro-

(56) References Cited

OTHER PUBLICATIONS matin integrity better than cryopreservation, Biology of Reproduction 85, 536-547 (2011) DOI 10.1095/biolreprod.111.091322.
Rogers, B. J., Importance of glycolysable substrates for in vitro capacitation of human spermatozoa, Biology of reproduction, (Dec. 1990) vol. 43, No. 6, pp. 1064-1069. Journal code: 0207224. ISSN: 0006-3363. L-ISSN: 0006-3363.
Tateno, Hiroyuki et al., Ca2+ ionophore A23187 can make mouse spermatozoa capable of fertilizing in vitro without activation of cAMP-dependent phosphorylation pathways, Proceedings of the National Academy of Sciences of the United States of America, (Nov. 12, 2013) vol. 110, No. 46, pp. 18543-18548,CODEN: PNASA6. ISSN: 0027-8424, DOI 10.1073/pnas.1317113110.
Urner, Francoise et al., Protein tyrosine phosphorylation in sperm during gamete interaction in the mouse: The influence of glucose, Biology of Reproduction 64, 1350-1357 (2001).
Vandevoort, C. A., Effects of glucose and other energy substrates on the hyperactivated motility of macaque sperm and the zona pellucida-induced acrosome reaction. Journal of andrology, (Jul.-Aug. 1995) vol. 16, No. 4, pp. 327-333, Journal code: 8106453. ISSN: 0196-3635. L-ISSN: 0196-3635.
Visconti, Pablo E., Roles of bicarbonate, cAMP, and protein tyrosine phosphorylation on capacitation and the spontaneous acrosome reaction of hamster sperm, Biology of Reproduction, (Jul. 1999) vol. 61, No. 1, pp. 76-84. print. CODEN: BIREBV. ISSN: 0006-3363.
Vizel, Ruth, et al., AKAP3 degradation in sperm capacitation is regulated by its tyrosine phosphorylation, Biochimica et Biophysica Acta, General Subjects (2015), 1850(9), 1912-1920,CODEN: BBGSB3; ISSN: 0304-4165, DOI 10.1016/j.bbagen.2015.06.005.
Williams, Andrew C. et al., The role of glucose in supporting motility and capacitation in human spermatozoa, J. of Andrology., vol. 22, No. 4, Jul./Aug. 2001, pp. 680-695.
Pre-office action interview communication dated May 1, 2019 for U.S. Appl. No. 16/282,204.
Instructions for the Use of AllGrad Wash, IFU-GALWV11, Dec. 3, 2018, LifeGlobal Group, Catalogue Nos. GALW-100, GALW-500, LifeGlobal Europe, Rue de la Presse 4, 1000 Brussels, Belgium; LifeGlobal Group, LLC, 393 Southview Rd., Guildford, CT 06437 US, http://www.LifeGlobalGroup.com (2 pages).
Amaral, Alexandra et al., (2013) Human Sperm Tail Proteome Suggest new Endogenous Metabolic Pathways, Molecular & Cellular Proteomics 12: 10.1074/mcp.M112.020552, 330-342.
Calvert, S.J., et al., (2018), Probing Human Sperm Metabolism Using 13C-Magnetic Resonance Spectroscopy, Molecular Human Reproduction, vol. 25, No. 1, pp. 30-41.
Piomboni, P., et al., The Role of Mitochondria in Energy Production for Human Sperm Motility, International Journal of Andrology, Apr. 2012;35(2):109-24. Epub Sep. 27, 2011.
Sperm Washing Medium with HSA, Catalog No. 9983, Fujifilm Irvine Scientific, Santa Ana, California 92705 USA, Copyright 2019.
Brackett, Benjamin et al., Analysis of factors involved in the in vitro production of bovine embryos, Theriogenology, vol. 39, Issue 1, Jan. 1993, pp. 43-64.
Cooper, et al., World Health Organization reference values for human semen characteristics, Human Reproduction Update, 16(3), pp. 231-245, 2009.
Cross, et al., Two simple methods for detecting acrosome-reacted human sperm. Gamete Res. 1986:15:213-26.
Gardner, David K. et al., Culture and transfer of human blastocysts increases implantation rates and reduces the need for multiple embryo transfers, Fertility and Sterility, vol. 69, No. 1, Jan. 1998.
Rogers, B. Jane et al., Analysis of Human Spermatozoal Fertilizing Ability Using Zona-Free Ova, Fertility and Sterility, vol. 32, No. 6, 664, Dec. 1979.
Vasan, S.S., Semen analysis and sperm function tests: How much to test?, Indian J. Urol. Jan.-Mar. 2011: 27(1):41-48.

METHODS FOR PROMOTING FERTILIZATION

CROSS-REFERENCE

This application claims the benefit of U.S. Provisional Application No. 62/773,471, filed Nov. 30, 2018, which application is incorporated herein by reference in its entirety.

BACKGROUND

Male factor is a contributing factor for ~50% of couples having difficulty conceiving. An important aspect of assisted reproduction is obtaining maximal function of male gametes (sperm) to help maximize fertilization. Accordingly, a need exists for media, compositions, and methods for increasing sperm function, e.g., to facilitate assisted reproduction.

SUMMARY

In some embodiments, provided herein is a method for promoting fertilization comprising: (a) incubating a mammalian sperm under energy depletion conditions for a time suitable to potentiate the mammalian sperm, (b) providing the potentiated mammalian sperm from step (a) with an effective amount of a first energy source and a second energy source in a serial manner, and (c) providing the mammalian sperm resulting from step (b) with access to an egg under conditions to promote fertilization.

In some embodiments, one or more sperm function selected from curvilinear velocity, amplitude of lateral head displacement, autophagy, sperm capacitation, percentage of hyperactivated sperm, percentage of intermediate motility sperm and percentage of hyperactivated sperm and intermediate motility sperm, is improved relative to a method wherein the potentiated sperm are provided with only one of first energy source and the second energy source or with the first energy source and the second energy source simultaneously. In some embodiments, the first energy source is a glycolytic energy source and the second energy source is a gluconeogenesis substrate, or the first energy source is the gluconeogenesis substrate and the second energy source is the glycolytic energy source.

In some embodiments, the method is performed in vitro. In some embodiments, step (c) is performed in vivo, in the reproductive tract of a female subject by intrauterine insemination (IUI) of the mammalian sperm from step (b). In some embodiments, providing the second energy source of step (b) is performed in vivo, in the reproductive tract of a female subject by intrauterine insemination (IUI) of the potentiated mammalian sperm provided with an effective amount of the first energy source. In some embodiments, the first energy source is a gluconeogenesis substrate that is pyruvate and the second energy source is a glycolytic energy source. In some embodiments, step (c) comprises incubating the mammalian sperm from step (b) with the egg, or injecting the mammalian sperm from step (b) into the cytoplasm of the egg to promote in vitro fertilization of the egg.

In some embodiments, promoting fertilization comprises generation of an embryo, wherein the embryo exhibits increased viability and/or improved implantation relative to an embryo generated by a suitable control sperm. In some embodiments, promoting fertilization comprises generation of an embryo which develops to at least a 2-cell developmental stage, a blastocyst developmental stage, or an offspring. In some embodiments, the mammalian sperm of step (a) is from an oligospermic subject or a subfertile subject. In some embodiments, the mammalian sperm of step (a) is a human, non-human primate, porcine, bovine, equine, ovine, canine, feline, or murine sperm. In some embodiments, the mammalian sperm of step (a) is a human sperm. In some embodiments, the mammalian sperm of step (a) is a sperm recovered from a non-cryogenic or cryogenic storage.

In some embodiments, the mammalian sperm of step (a) is provided as a pool of two or more ejaculates. In some embodiments, the mammalian sperm of step (a) is enriched from semen prior to step (a) by density gradient centrifugation, swim up, or microfluidics. In some embodiments, the method is performed at an osmolality ranging from 200-280 mOsm/kg. In some embodiments, step (b) further comprises providing the mammalian sperm with one or more components upstream or downstream of glycolysis in combination with at least the first energy source or the second energy source. In some embodiments, the first energy source is selected from: (i) glucose or (ii) pyruvate; and the second energy source is selected from: (i) glucose or (ii) pyruvate, and wherein the first and second energy source are different. In some embodiments, the energy depletion is for at least 10 minutes.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference. For example, all publications and patents mentioned herein are incorporated herein by reference in their entirety for the purpose of describing and disclosing the kits, compositions, and methodologies that are described in the publications, which might be used in connection with the methods, kits, and compositions described herein. The documents discussed herein are provided solely for their disclosure prior to the filing date of the present application. Nothing herein is to be construed as an admission that the inventors described herein are not entitled to antedate such disclosure by virtue of prior invention or for any other reason.

DETAILED DESCRIPTION OF THE INVENTION

Figure 1:
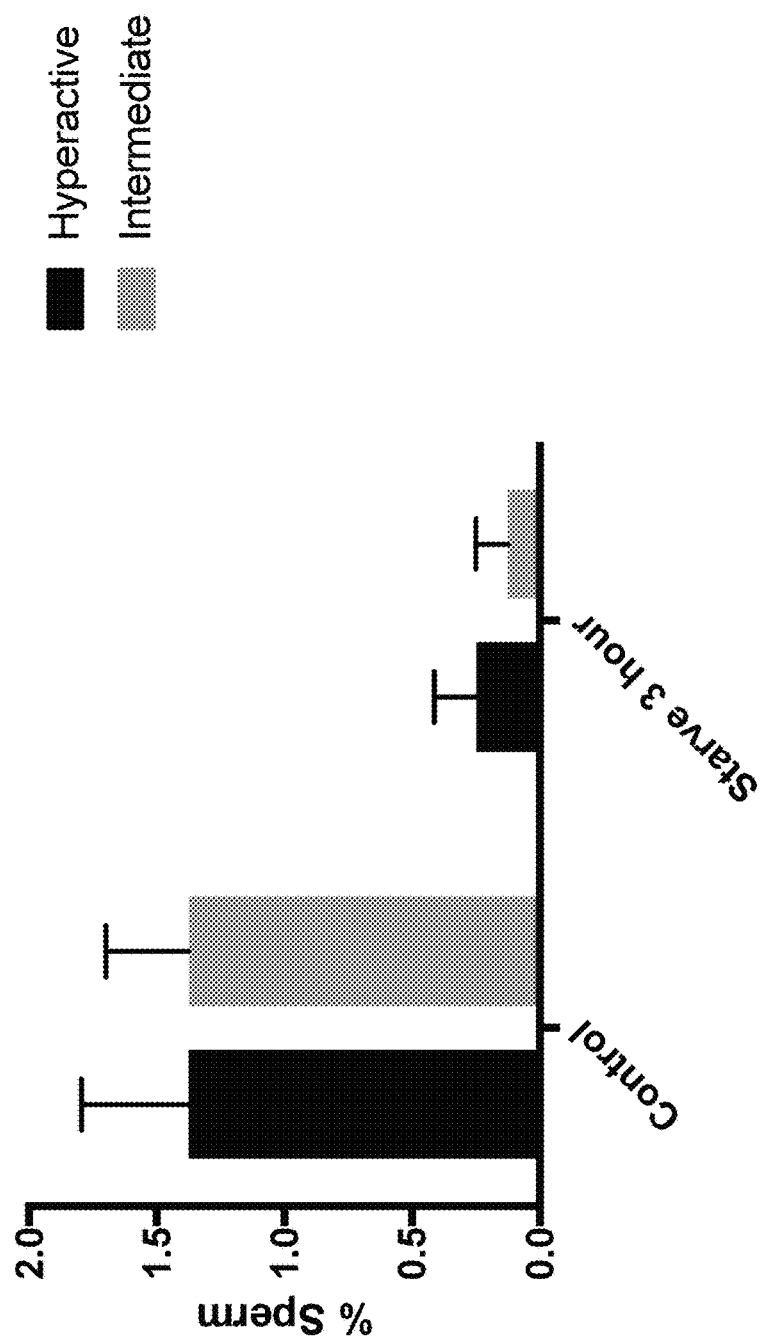
FIG. 1 is a bar graph of the percentage of hyperactive and intermediate motility sperm in control and starved (glucose, pyruvate, and lactate-free) conditions.

Male factor is a contributing factor for ~50% of couples having difficulty conceiving. Low sperm count is a recognized factor in male infertility. The World Health Organization defines low sperm count (oligospermia) as less than 15 million sperm per milliliter (Cooper et al., Human Reproduction Update, 16(3), 231-245, 2009). Other factors contributing to male infertility or subfertility include low motility or abnormal morphology. An important aspect of assisted reproduction is obtaining maximal function of male gametes (sperm) to help maximize fertilization. Before fertilization, sperm must go through a series of changes to be able to fertilize the egg, a process called sperm capacitation. In vitro capacitation media, includes three components (albumin, calcium and bicarbonate) and initiate sperm capacitation. Sperm initially swim progressively with an almost symmetrical flagellar movement. After different periods of time, which depend on the species, the straight sperm movement is replaced by an in-place helical movement known as "hyperactivation". While methods for activating sperm exist, they fail to achieve maximal sperm activation and therefore do not adequately address the impact of male factor in infertility. Accordingly, a need exists for media, compositions, and methods for increasing sperm function, e.g., to facilitate assisted reproduction.

The present disclosure provides, inter alia, methods for increasing sperm function, preparations of sperm, methods of fertilization, and articles of manufacture, e.g., useful for performing methods provided by the disclosure. The invention is based, at least in part, on Applicant's surprising discovery that staged reintroduction of different energy sources after a period of starvation achieves superior activation of sperm.

Definitions

To facilitate an understanding of the present disclosure, a number of terms and phrases are defined below.

The terms "increased"/'increase", "increasing" or "enhance" or "promote" are all used herein to generally mean an increase; for the avoidance of doubt, the terms "increased", "increase", or "enhance", mean an increase of at least 5%, e.g., at least 10% as compared to a suitable control, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a suitable control, or at least about a 2-fold, or at least about a 3-fold, or at least about a 4-fold, or at least about a 5-fold or at least about a 10-fold increase, or any increase between 2-fold and 10-fold or greater as compared to a suitable control. The increase can be, for example, at least 10%, at least 20%, at least 30%, at least 40% or more, and is preferably to a level accepted as within the range of normal sperm from a mammalian male subject without a given disease (e.g., male infertility, due to abnormal sperm function or oligospermia).

The terms, "decrease", "reduce", "reduction", "lower" or "lowering," or "inhibit" are all used herein generally to mean a decrease. For example, "decrease", "reduce", "reduction", or "inhibit" means a decrease by at least 5%, e.g., 10% as compared to a suitable control, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a suitable control), or any decrease between 10-100% as compared to a suitable control. The decrease can be, for example, at least 10%, at least 20%, at least 30%, at least 40% or more, than the range of normal for an individual without a given disease.

As used herein, the term "effective amount" means the total amount of the active component(s) of a first energy source or a second energy source that is sufficient to cause a change on a detectable function of the mammalian sperm (e.g., sperm motility, curvilinear velocity, amplitude of lateral head displacement, autophagy, sperm capacitation, percentage of hyperactivated sperm, percentage of intermediate motility sperm and percentage of hyperactivated sperm and intermediate motility sperm, ability to fertilize an egg, and generation of an embryo). When applied to an individual energy source, administered alone, the term refers to that energy source alone. When applied to a combination, the term refers to combined amounts of the first energy source and the second energy source that result in the effect, whether administered in combination, serially or simultaneously.

The term "an effective amount" includes within its meaning a sufficient amount of an energy source (e.g., a gluconeogenesis substrate or glycolytic energy source) to provide the desired effect. As it relates to the present disclosure, the desired effect can be increase in one or more sperm function or increase in fertilization. The exact amount required will vary depending on factors such as the mammalian sperm species being treated, the age and general condition of the male subject from whom the mammalian sperm is obtained, for example if the sperm is obtained from a sub-fertile mammalian subject. Thus, it is not possible to specify an exact "effective amount". However, for any given case, an appropriate "effective amount" may be determined by one of ordinary skill in the art using only routine experimentation.

The term "spermatozoon" refers to a live reproductive cell from a male mammal. The term "spermatozoa" refers to a plurality of live male reproductive cells. Unless required otherwise by context, the plural and singular forms are interchangeable. The term "sperm" is used as an abbreviation and refers to at least one spermatozoon.

As used herein, the term "ability to fertilize an egg" refers to ability of a sperm (e.g., mammalian sperm) to penetrate an unfertilized egg (ovum) resulting in combination of their genetic material resulting in the formation of a zygote. As it relates to the present disclosure, the "ability to fertilize" an egg can be ability to fertilize in vitro and/or in vivo. In some embodiments, ability to fertilize in vitro comprises fertilization by Intracytoplasmic sperm injection (ICSI).

The term "embryo" is used herein to refer both to the zygote that is formed upon fertilization of an unfertilized egg by a mammalian sperm, to form a diploid totipotent cell, e.g. a fertilized egg and to the embryo that undergoes subsequent cell divisions to develop to 2-cell stage or greater (e.g., 4-cell stage, 16-cell stage, 32-cell stage, the blastocyst stage (with differentiated trophectoderm and inner cell mass) or development into an offspring).

As used herein, the term "ability to develop" refers to the ability or capacity of an embryo to grow or develop. The terms may refer to the ability or capacity of an embryo to reach at least the 2-cell developmental stage, the blastocyst developmental stage, implant into the uterus, to develop to a full offspring, or be born live. The term "offspring" as used herein refers to a progeny of a parent, wherein the progeny is an unborn fetus or a newborn.

The term "blastocyst" refers to an embryo, five or six days after fertilization, having an inner cell mass, an outer cell layer called the trophectoderm, and a fluid-filled blastocele cavity containing the inner cell mass from which the whole of the embryo is derived. The trophectoderm is the precursor to the placenta. The blastocyst is surrounded by the zona pellucida which is subsequently shed when the blastocyst "hatches." The zona pellucida, composed of a glycoprotein coat, surrounds the oocyte from the one-cell stage to the blastocyst stage of development. Prior to embryo attachment and implantation, the zona pellucida is shed from the embryo by a number of mechanisms including proteolytic degradation. The zona pellucida functions initially to prevent entry into the oocyte by more than one sperm, then later to prevent premature adhesion of the embryo before its arrival into the uterus.

As used herein, the term "enriched" refers to a composition or fraction or preparation wherein an object species has been partially purified such that the concentration of the object species is substantially higher than the naturally occurring level of the species in a finished product or preparation without enrichment.

Some numerical values disclosed throughout are referred to as, for example, "X is at least or at least about 100; or 200 [or any numerical number]." This numerical value includes the number itself and all of the following:

i. X is at least 100;
  ii. X is at least 200;
  iii. X is at least about 100; and
  iv. X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, "X is administered on or on about day 1 to 2; or 2 to 3 [or any numerical range]." This range includes the numbers themselves (e.g., the endpoints of the range) and all of the following:

i. X being administered on between day 1 and day 2;
  ii. X being administered on between day 2 and day 3;
  iii. X being administered on between about day 1 and day 2;
  iv. X being administered on between about day 2 and day 3;
  v. X being administered on between day 1 and about day 2;
  vi. X being administered on between day 2 and about day 3;
  vii. X being administered on between day 1 and about day 2; and
  viii. X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

Sperm Function

In some embodiments, provided herein is a method for increasing sperm function. The method comprises incubating a mammalian sperm under energy depletion for a time suitable to potentiate the mammalian sperm, providing the potentiated mammalian sperm with an effective amount of a first energy source selected from: (i) a glycolytic energy source or (ii) a gluconeogenesis substrate, and subsequently providing the mammalian sperm from step (b) with an effective amount of a second energy source, selected from: (i) the glycolytic energy source or (ii) the gluconeogenesis substrate, wherein the energy source provided is not the one selected as first energy source, thereby inducing increased sperm function compared to a suitable control sperm. In some embodiments, the method is performed in vitro. In some embodiments, the providing of the second energy source is performed in vivo, for example, by cervival or intrauterine insemination of the sperm which has been previously incubated under energy depletion and provided a first energy source. Increased sperm function includes one or more of: increased motility such as the percentage of sperm in a population exhibiting hyperactivation and/or intermediate motility as assessed by CASAnova (see Goodson et al., 2017, Biol. Reprod. 97:698-708; doi:10.1093/biolre/iox120), increased autophagy, increased capacitation, and increased rates of fertilization, e.g., development to at least two cells, blastocyst development, or live birth. Accordingly, in some embodiments, sperm function can be sperm motility, curvilinear velocity, amplitude of lateral head displacement, autophagy, sperm capacitation, percentage of hyperactivated sperm, percentage of intermediate motility sperm and percentage of hyperactivated sperm and intermediate motility sperm, ability to fertilize an egg, generation of an embryo. In some embodiments, the embryo generated by the sperm with increased function comprises one or more characteristics selected from increased viability, increased implantation, increased ability to develop to a at least a 2-cell developmental stage, blastocyst developmental stage or an offspring.

In some embodiments, the first and second energy sources are provided in a serial manner (e.g., providing a first energy source and subsequently providing a second energy source). In some embodiments, the first and second energy sources are provided simultaneously. An increase in one or more sperm functions, as contemplated herein, constitutes an increase in the one or more sperm functions relative to a suitable control sperm. In some embodiments, the one or more sperm functions can be increased by at least or at least about 5%, 10%, 20%, 30%, 40%, 50%, 60%, 75%, 80%, 90%, or 100%, 200%, 300% or more. In some embodiments, the one or more sperm functions can be increased by from 10% to 200%, from 25% to 150%, from 50% to 100%, or from 70% to 90%.

Provided herein, are methods to increase sperm function and preparation of sperm comprising increased function relative to a suitable control sperm. As it relates to the present disclosure, sperm "activity" and/or "function" encompass physiological processes such as, for example, sperm motility, sperm tropism (namely, the tendency of sperm to move towards or away from certain stimuli), and ability to fertilize an egg. The terms "activity" and/or "function" can further include processes which occur prior to, during fertilization and/or interaction with the egg (or membranes/layers thereof)—such processes may include, for example sperm capacitation and acrosomal activity, and/or processes after fertilization of egg, for example, formation of an embryo. In some embodiments, the embryo exhibits increased (longer) viability, improved implantation, and/or ability to develop to a 2-cell stage, a blastocyst, or to an offspring resulting in live birth.

Exemplary methods to measure an increase in sperm function may be assessed by motility, mucus penetration, oocyte fertilization or subsequent embryonic development and the like. Methods to determine sperm function are well known in the art, see for example, SS. Vasan Indian J Urol. 2011 January-March; 27(1): 41-48.

Sperm Motility

With regard to sperm motility, one of skill will appreciate that the term "motility" not only relates to general movement, but may be applied to other aspects of motility such as, for example, the speed of movement of a sperm cell and/or any increase or decrease in the proportion of moving sperm cells in any given population. As such, the methods disclosed herein may be used not only to increase sperm motility, but also to increase the speed of movement of a sperm cell and/or the proportion (percentage) of moving cells in any given population of sperm.

Motility of sperm is expressed as the total percent of motile sperm, or the velocity of sperm that are motile. These measurements may be made by a variety of assays, but are conveniently assayed in one of two ways. Either a subjective visual determination is made using a phase contrast microscope when the sperm are placed in a hemocytometer or on a microscope slide, or a computer assisted semen analyzer is used. Under phase contrast microscopy, motile and total sperm counts are made and speed is assessed as fast, medium or slow. A second method of assessing sperm motility is by using a computer assisted semen analyzer (Hamilton Thorn, Beverly, Mass.), the motility characteristics of individual sperm cells in a sample are objectively determined. Briefly, a sperm sample is placed onto a slide or chamber designed for the analyzer. The analyzer tracks individual sperm cells and determines motility and velocity of the sperm. Data is expressed as percent motile, and measurements are obtained for path velocity and track speed as well.

Accordingly, the term "motility" encompasses percentage of motile sperm which can be the percentage of the total number of sperm assessed that fall within all World Health Organization (WHO) categories of motility except the category designated "no motility" regardless of velocity or directionality as discussed in Cooper et al. Human Reproduction update, Vol 16, No 3 pp 231-245, 2010. Manual counting classifies sperm cells into 4 categories (immotile, locally motile, non linear and linear motile) using qualitative subjective criteria of selection.

The term "motility" encompasses percentage of motile sperm i.e., the percentage of total number of sperm assessed in a population exhibiting progressive motility, hyperactivated motility and/or intermediate motility based on Computer assisted sperm analysis (For example, as assessed by CASAnova; see Goodson et al, 2017, Biol. Reprod. 97:698-708).

The methods disclosed herein can increase percentage of progressive motility sperm, i.e., percentage of sperm exhibiting linear movement from one point to another, with turns of the head of less than 90 degrees from sperm that are otherwise non-progressive, i.e., sperm that move but do not make forward progression. In some embodiments, the methods disclosed herein can increase percentage of intermediate motility sperm. Intermediate motility sperm is characterized by movement that is similar to progressive vigorous motility, but has a larger variance from the path and turns of the sperm head of approximately 90 degrees, such as an oscillating movement. In some embodiments, the increased motility comprises increase in percentage of activated hyperactive sperm, also known as hyperactivated sperm. Hyperactivated sperm motility is characterized by sperm that have a high amplitude, asymmetrical beating pattern of the flagellum. Hyperactivated motility is characterized by vigorous movement with many seemingly random variations without a well-defined progressive path and turns of the sperm head of greater than 90 degrees. Hyperactivated sperm motility is more vigorous and short term than progressive motility. Biologically, hyperactivated sperm motility is important to enable sperm to traverse the egg outer investments prior to fertilizing the mature egg. In some embodiments, the methods disclosed herein can increase percentage of hyperactivated sperm and intermediate motility sperm in a given population of sperm.

It should be understood that other standardized measures of sperm motility parameters can also be used. Other measures of sperm motility include "velocity" and "linearity" which can be assessed using automatic semen analyzers. In some embodiments, the methods disclosed herein can increase sperm function comprising increase in average path velocity (VAP), straight-line velocity (VSL), curvilinear velocity (VCL), amplitude of lateral head displacement (ALH) and beat cross frequency (BCF) or other movement parameters of the sperm including parameters known to those of skill in the art. Curvilinear velocity (VCL) is the measure of the rate of travel of the centroid of the sperm head over a given time period. Average path velocity (VAP) is the velocity along the average path of the spermatozoon. Straight-line velocity (VSL) is the linear or progressive velocity of the cell. Linearity of forward progression (LIN) is the ratio of VSL to VCL and is expressed as percentage. Amplitude of lateral head displacement (ALH) of the sperm head is calculated from the amplitude of its lateral deviation about the cell's axis of progression or average path. Methods of measuring sperm motility by CASA are well known in the art, see for example, WO2012061578A2. An increase in sperm motility, as contemplated herein, constitutes anincrease in the motility of sperm relative to a suitable control sperm.

In some embodiments sperm with increased motility are provided that are the product of a process comprising incubating sperm in energy depletion conditions to potentiate the sperm, followed by providing the potentiated sperm with a first energy source and a second energy source. In some embodiments, the first and second energy sources are provided simultaneously. In some embodiments, the first and second energy sources are provided serially. In some embodiments, the increase in sperm motility can be more than about 10%, 20%, 30%, 40%, 50%, 60%, 70%, 80%, 90%, or 99% relative to a suitable control sperm. In some embodiments, the increase in sperm motility can be at least 5%, at least 10%, at least 20%, at least 30%, at least 40%, at least 50%, at least 60%, at least 70%, at least 80%, at least 90%, or at least 95%. In some embodiments, the increase in sperm motility can be by a factor of at least 10, at least 100, at least 1,000, at least 10,000. In some embodiments, the sperm motility can be increased by from 10% to 200%, from 25% to 150%, from 50% to 100%, or from 70% to 90%. In some embodiments, the increased sperm function or increased sperm motility can be an increase in percentage of hyperactivated sperm. In some embodiments, the increased sperm function or increase in sperm motility can be an increase in percentage of intermediate motility sperm. In some embodiments, the increased sperm function or increased sperm motility can be an increase in percentage of progressive motility sperm. In some embodiments, the increased sperm function or increased sperm motility can be an increase in percentage of the hyperactivated sperm and intermediate motility sperm. In some embodiments, the level of hyperactivated sperm, progressive motililty sperm, intermediate motility sperm or a combination thereof is increased so that hyperactivated sperm, progressive motililty sperm, intermediate motility sperm or a combination thereof comprise at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. An increase in sperm motility is indicative of increased sperm function.

Sperm Capacitation

In some embodiments the increased sperm function comprises an increase in sperm capacitation. "Sperm capacitation" refers to the sperm having the ability to undergo acrosomal exocytosis and binding to and penetrating through the zona pellucida of an unfertilized egg. Completion of capacitation is manifested by the ability of sperm to bind to the zona pellucida and to undergo ligand-induced acrosomal reaction. Methods to determine sperm capacitation are known in the art, for example, the most common sperm-zona pellucida binding tests currently utilized are the hemizona assay (or HZA) and a competitive intact-zona binding assay. A hemizona assay measures the ability of sperm to undergo capacitation and bind to an oocyte. Sperm is incubated with dead oocytes which are surrounded by the zona pellucida, an acellular coating of oocytes. Capacitated sperm bind to the zona and the number of sperm binding is counted microscopically. This number correlates with the number of normal capacitated sperm in a sample and with fertility of a sperm sample. For example, see Cross N L et al. Gamete Res. 1986; 15:213-26.

In some embodiments, sperm with increased capacitation are provided that are the product of a process comprising incubating sperm in energy depletion conditions to potentiate the sperm, followed by providing the potentiated sperm with a first energy source and a second energy source simultaneously, or serially. In some embodiments, the increase in sperm capacitation can be more than about 10%, 20%, 30%, 40%, 50%, 60%, 70%, 80%, 90%, or 99% relative to a suitable control sperm. In some embodiments, the increase in sperm capacitation can be at least 5%, at least 10%, at least 20%, at least 30%, at least 40%, at least 50%, at least 60%, at least 70%, at least 80%, at least 90%, or at least 95%. In some embodiments, the increase in sperm capacitation can be by a factor of at least 10, at least 100, at least 1,000, at least 10,000. In some embodiments, the sperm capacitation can be increased by from 10% to 200%, from 25% to 150%, from 50% to 100%, or from 70% to 90%. In some embodiments, the level of sperm capacitation is increased so that capacitated sperm can comprise at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% more of the total sperm in a preparation. An increase in sperm capacitation is indicative of increased sperm function.

Fertilizing Ability

In some embodiments, the sperm function comprises ability of the sperm to fertilize an egg. The fertilizing ability of a sperm can be determined, for example, by a sperm penetration assay. The spermatozoa penetration assay (SPA) utilizes the golden hamster egg, which is unusual in that removal of its zona pellucida results in loss of all species specificity to egg penetration. This test is conducted to determine the ability of sperm to penetrate into the oocyte (Rogers et al., Fert. Ster. 32:664, 1979). Briefly, commercially available zona free hamster oocytes can be used (Fertility Technologies, Natick, Mass.). Hamster oocytes are suitable in this assay for sperm of any species. Sperm are incubated for 3 hours with the hamster oocytes. Following incubation, oocytes are stained with acetolacmoid or equivalent stain and the number of sperm penetrating each oocyte is counted microscopically. Another parameter of sperm fertilizing ability is the ability to penetrate cervical mucus. This penetration test can be done either in vitro or in vivo. Briefly, in vitro, a commercial kit containing cervical mucus (Tru-Trax, Fertility Technologies, Natick, Mass.), typically bovine cervical mucus, is prepared. Sperm are placed at one end of the track and the distance that sperm have penetrated into the mucus after a given time period is determined. Alternatively, sperm penetration of mucus may be measured in vivo in women. In an embodiment sperm with increased fertilizing ability are provided that are the product of a process comprising incubating sperm in energy depletion conditions to potentiate the sperm, followed by providing the potentiated sperm with a first energy source and a second energy source simultaneously, or serially. In some embodiments, the increase in fertilizing ability can be more than about 10%, 20%, 30%, 40%, 50%, 60%, 70%, 80%, 90%, or 99% relative to a suitable control sperm. In some embodiments, the increase in fertilizing ability can be at least 5%, at least 10%, at least 20%, at least 30%, at least 40%, at least 50%, at least 60%, at least 70%, at least 80%, at least 90%, or at least 95%. In some embodiments, the increase in fertilizing ability can be by a factor of at least 10, at least 100, at least 1,000, at least 10,000. In some embodiments, the fertilizing ability can be increased by from 10% to 200%, from 25% to 150%, from 50% to 100%, or from 70% to 90%. In some embodiments, the level of fertilizing ability is increased so that the number of sperm able to fertilize an egg is at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. An increase in fertilizing ability is indicative of increased sperm function and increased fertilization.

Generating Embryos

In some embodiments, sperm function comprises generating an embryo. In some embodiments, the sperm with increased function prepared by methods herein is provided access to an egg to promote fertilization, wherein promoting fertilization can comprise generation of an embryo. In some embodiments, the sperm with increased function prepared by the methods herein is provided access to an egg in vitro, thereby generating the embryo in vitro. In some embodiments, the sperm with increased function prepared by the methods disclosed herein is provided access to an egg in vivo by IUI of the sperm, thereby generating the embryo in vivo. In some embodiments, the sperm which has been incubated under energy deletion conditions and provided with first energy source is inseminated in the reproductive tract of a female subject such that providing the second energy source and providing access to an egg to generate an embryo occurs in vivo. In some embodiments, where the embryo is generated in vitro, the embryo can be cryopreserved for later use or can be further cultured in vitro to enable embryonic development. In some embodiments, the embryo is developed to at least a two cell stage prior to cryopreserving and/or implantation into a female subject. In some embodiments, the embryo is developed to a developmental stage greater than the two-cell stage in vitro prior to further processing. In some embodiments, the embryo is developed to a blastocyst stage in vitro prior to further processing (e.g., cryopreservation or implantation into a female subject to develop into a full offspring). For in vitro incubation and culture of embryos during via assisted reproductive technologies (ART) procedures, a range of suitable media are available, the types and compositions of which are well known to those of skill in the art. Preferably the culture medium contains at least water, salts, nutrients, essential amino acids, vitamins and hormones, and may also include one or more growth factors. A variety of suitable culture media is commercially available, for example Earle's media, Ham's F10 media and human tubal fluid (HTF) media. The present disclosure also contemplates the co-culture in vitro of embryos on a layer of 'feeder cells' by methods known in the art. Appropriate 'feeder cells' for co-culture may include, for example, bovine oviductal cells or human tubal epithelial cells.

Those of skill in the art will appreciate that the advantages offered by the sperm with increased function prepared by the methods disclosed herein are not limited to increasing fertilization. Rather the methods and preparation of the present invention are equally applicable as treatment to promote fertilization, whether the embryos are produced in vitro via assisted reproductive technologies (ART) or in the reproductive tract of the animal. The methods of the present invention are applicable to improving fertilization, embryo viability, embryo implantation and pregnancy rates in assisted or otherwise unassisted pregnancies. Embodiments of the present disclosure also provide for methods of increasing the fertilizing ability of sperm in male animals.

In the context of this specification, the terms "embryo with increased viability" and "embryo with longer viability" mean an increase or enhancement in the likelihood of survival of an embryo(s) which has been generated by the mammalian sperm of the methods and preparation disclosed herein, for example, a mammalian sperm with one or more increased sperm function, compared to the likelihood of survival of an embryo(s) which has been generated by a suitable control sperm. In some embodiments, the embryo is generated by an assisted reproductive technology e.g., IVF or ICSI. In some embodiments, the embryo is generated in vivo in the reproductive tract of a female mammalian subject by artificial insemination.

For the purposes of the present disclosure, embryo viability may be reflected in a number of indicators. For example, increased embryo viability may result in increased embryo implantation rates following fertilization, decreased pre- and post-implantation embryo lethality, increased clinical pregnancy rates or increased birth rates. The present disclosure therefore also relates to methods of preventing apoptosis or retarded development in embryos and to methods of increasing pregnancy rates in animals. The embryo viability can refer to viability of an embryo in vitro or in vivo.

In some embodiments, sperm with ability to generate an embryo with increased viability is provided that are the product of a process comprising incubating sperm in an energy depletion conditions to potentiate the sperm, followed by providing the potentiated sperm with a first energy source and a second energy source simultaneously, or serially. In some embodiments, providing the sperm with increased function access to an egg promotes fertilization. In some embodiments, promoting fertilization comprises generation of an embryo(s) with increased viability. In some embodiments, the increase in viability of embryo generated by the sperm prepared by methods herein upon access to an egg can be more than about 10%, 20%, 30%, 40%, 50%, 60%, 70%, 80%, 90%, or 99% relative to an embryo generated by a suitable control sperm. In some embodiments, the increase in embryo viability can be at least 5%, at least 10%, at least 20%, at least 30%, at least 40%, at least 50%, at least 60%, at least 70%, at least 80%, at least 90%, or at least 95%. In some embodiments, the increase in embryo viability can be by a factor of at least 10, at least 100, at least 1,000, at least 10,000. In some embodiments, the embryo viability can be increased by from 10% to 200%, from 25% to 150%, from 50% to 100%, or from 70% to 90%. In some embodiments, the level of sperms that can generate an embryo with increased viability is at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. Generation of an embryo with increased viability is indicative of increased sperm function and/or increased fertilization.

Typically the cleavage stage of embryo occurs during the first three days of culture. The in vitro generated embryo is transferred to a female subject by embryo transfer. "Embryo transfer" is the procedure in which one or more embryos and/or blastocysts are placed into the uterus or fallopian tubes. In the traditional IVF process, embryos are transferred to the uterine cavity two days after fertilization when each embryo is at the four (4) cell stage or three days after fertilization when the embryo is at the eight (8) cell stage. It has been recognized that it may be desirable to use embryos at the blastocyst stage when reached at day five to seven of culture. The present disclosure allows for embryo transfer at any time along the spectrum of embryo/blastocyst development. Through visual observation, such as by with the use of microscopy, blastocysts or embryos are considered ready to be transferred to the uterus when the blastoceol cavity is clearly evident and comprises greater than 50% of the volume of the embryo. In an in vivo environment, this stage would normally be achieved four to five days after fertilization, soon after the embryo has traversed the fallopian tube and arrives in the uterus. Embryonic developmental stage can be determined by visual observation of the embryo using microscopy (for example, Nikon Eclipse TE 2000-S microscope), the embryo will display certain determined physical or morphological features simultaneously before it is implanted into the uterus. The state of blastocyst maturity will be determined to be the range II AB-VI AA according to classification of Gardner et al, 1998.

The methods disclosed herein result in generation of embryos with increased rate of progressing to 2-cell developmental stage, blastocyst developmental stage, or development to an offspring and live birth. In some embodiments, sperm which can generate an embryo with ability to develop through normal developmental stages (e.g., 2 cell stage, blastocyst stage, development into an offspring and live birth) is provided that are the product of a process comprising incubating sperm in an energy depletion conditions to potentiate the sperm, followed by providing the potentiated sperm with a first energy source and a second energy source simultaneously, or serially. In some embodiments, providing the sperm with increased function access to an egg promotes fertilization. In some embodiments, promoting fertilization comprises generation of embryos with increased ability to develop through normal developmental stages (e.g., 2 cell stage, blastocyst stage, development into an offspring and live birth). In some embodiments, increase in rate of an embryo progressing through normal developmental stages, generated by the sperm prepared by methods can be more than about 10%, 20%, 30%, 40%, 50%, 60%, 70%, 80%, 90%, or 99% relative to an embryo generated by suitable control sperm. In some embodiments, the increase in rate of an embryo progressing through normal developmental stages can be at least 5%, at least 10%, at least 20%, at least 30%, at least 40%, at least 50%, at least 60%, at least 70%, at least 80%, at least 90%, or at least 95%. In some embodiments, the increase in rate of an embryo progressing through normal developmental stages can be by a factor of at least 10, at least 100, at least 1,000, at least 10,000. In some embodiments, the rate of embryo progressing through normal developmental stages can be increased by from 10% to 200%, from 25% to 150%, from 50% to 100%, or from 70% to 90%. In some embodiments, the level of sperms that can generate an embryo with ability to progress through normal developmental stages is at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. Generation of an embryo with ability to progress through one or more normal developmental stages is indicative of increased sperm function and/or increased fertilization.

In vivo, an embryo attaches or implants to a wall of the uterus, creates a placenta, and develops into a fetal offspring during gestation until childbirth. Testing to determine whether one or more embryos have implanted into the endometrium, i.e, whether the procedure has resulted in successful pregnancy inception, is performed two weeks after transfer using blood tests on b-hCG (human chorionic gonadotropin), for example, and other techniques commonly known in the art. U.S. Pat. No. 4,315,908 to Zer et al. sets forth a method for detecting hCG in the urine by radioimmunoassay. U.S. Pat. No. 8,163,508 to O'Connor et al. provides a method and a kit for predicting pregnancy in a subject by hCG method by determining the amount of an early pregnancy associated isoform of hCG in a sample. Such methods of diagnosis and others are useful within the scope of the disclosure.

In some embodiments, sperm with ability to generate an embryo with improved implantation rate or improved rate of pregnancy is provided that are the product of a process comprising incubating sperm in an energy depletion conditions to potentiate the sperm, followed by providing the potentiated sperm with a first energy source and a second energy source simultaneously, or serially. In some embodiments, providing the sperm with increased function access to an egg promotes fertilization. In some embodiments, promoting fertilization comprises generation of an embryo with improved implantation rate or improved rate of pregnancy. In some embodiments, the increase in implantation rate of an embryo generated by the sperm prepared by methods herein or pregnancy rate upon implantation of an embryo can be more than about 10%, 20%, 30%, 40%, 50%, 60%, 70%, 80%, 90%, or 99% relative to an embryo generated by a suitable control sperm. In some embodiments, the increase in an embryo implantation rate or pregnancy rate can be at least 5%, at least 10%, at least 20%, at least 30%, at least 40%, at least 50%, at least 60%, at least 70%, at least 80%, at least 90%, or at least 95%. In some embodiments, the increase in rate of embryo implantation or rate of pregnancy can be by a factor of at least 10, at least 100, at least 1,000, at least 10,000. In some embodiments, the embryo implantation or pregnancy rate can be increased by from 10% to 200%, from 25% to 150%, from 50% to 100%, or from 70% to 90%. In some embodiments, the level of sperms that can generate an embryo with increased implantation rate or improved pregnancy rate is at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. Generation of embryos with improved implantation (i.e., increased rate of implantation) or increased pregnancy rate upon implantation is indicative of increased sperm function and/or increased fertilization.

Autophagy

In some embodiments, the increased sperm function comprises an increase in autophagy. Methods to determine an increase in autophagy are known in the art. For example, an increase in autophagy can be determined by increase in one or more of autophagy marker proteins. The detection of increase in marker protein can be done by conventional methods such as immunoblotting. Non-limiting examples of autophagy marker proteins include, Atg 5, Atg 16, p62, LC3-II, AMPK, m-TOR and Beclin 1. LC3-II has been widely used to study autophagy and it has been considered as an autophagosomal marker in mammals. A ratio of LC3-II/LC3-I can be used as a determinant of increase in autophagy. An increase in levels of one or more autophagy marker proteins (e.g., Atg 5, Atg 16, p62 and LC3-II, AMPK, m-TOR and Beclin 1), and/or an increase in ratio of LC3-II/LC3-I can be indicative of increase in sperm function.

In some embodiments, sperm with increased autophagy are provided that are the product of a process comprising incubating sperm in energy depletion conditions to potentiate the sperm, followed by providing the potentiated sperm with a first energy source and a second energy source simultaneously, or serially. In some embodiments, the increase in autophagy can be more than about 10%, 20%, 30%, 40%, 50%, 60%, 70%, 80%, 90%, or 99% relative to a suitable control sperm. In some embodiments, the increase in sperm autophagy can be at least 5%, at least 10%, at least 20%, at least 30%, at least 40%, at least 50%, at least 60%, at least 70%, at least 80%, at least 90%, or at least 95%. In some embodiments, the increase in sperm autophagy can be by a factor of at least 10, at least 100, at least 1,000, at least 10,000. In some embodiments, the sperm autophagy can be increased by from 10% to 200%, from 25% to 150%, from 50% to 100%, or from 70% to 90%. In some embodiments, the level of sperm autophagy is increased so that sperm with increased autophagy can comprise at least about 5%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20%, 25%, 30%, 35%, 40%, 50% or more of the total sperm in a preparation. An increase in sperm autophagy is indicative of increased sperm function.

Starvation

"Energy depletion" means suppressing or restricting the energetic output of a cell whether by depletion, reduction (below an effective amount), or removal of such energy sources or inhibition of enzymatic or import machinery. In some embodiments one or more of glycolysis, gluconeogenesis, Kreb's cycle, or oxidative phosphorylation are inhibited in the energy depletion and, in particular embodiments, the energy depletion includes glycolytic energy depletion. Exemplary conditions of glycolytic energy depletion include removing substantially all of glycolytically-liable sugar, such as glucose (other embodiments can include, mannose, fructose, dextrose, sucrose, and combinations thereof, including combinations with glucose), in the sperm's medium or reducing the concentration of glycolytically-liable sugar, or using inhibitors of glycolysis, gluconeogenesis, or importers of glycolytically-liable sugars. As glucose is a primary energy source of sperm, in preferred embodiments, the energy depletion is glucose energy depletion (including starvation), which further entails depletion (including starvation) of gluconeogenesis substrates (including, e.g., pyruvate), and Kreb's cycle substrates (acetyl CoA, citrate, isocitrate, alpha-ketoglutarate, succinyl-CoA, succinate, fumarate, malate, and oxaloacetate).

In some embodiments, the energy depletion comprises a low glucose concentration, e.g., less than about: 0.5, 0.4, 0.3, 0.2, 0.1, 0.09, 0.08, 0.07, 0.06, 0.05, 0.04, 0.03, mM glucose, or less, such as less than about: 0.02 or 0.01 mM, e.g., less than about 0.01 mM. In some embodiments the energy depletion means a substantially glucose-free condition. The invention provides methods entailing staged provision of effective amounts of first and second energy sources and the skilled artisan will appreciate that in some embodiments encompassed within the invention, sub-effective amounts of a glycolytic energy source are an energy depletion and, for example, the foregoing low glucose concentrations can be employed in such embodiments as an energy depletion.

In some embodiments, the energy depletion comprises a low pyruvate concentration, e.g., less than about 0.15, 0.10, 0.09, 0.08, 0.07, 0.06, 0.05, 0.04, 0.03, 0.02, 0.01, 0.005, 0.003, 0.002 mM, or less. In some embodiments the energy depletion means a substantially pyruvate-free condition. As noted above and exemplified with glucose for a glycolytic energy source, the skilled artisan will also appreciate that in some embodiments encompassed within the invention sub-effective amounts of a gluconeogenesis substrate are an energy depletion and, for example, the foregoing low pyruvate concentrations can be employed in such embodiments as an energy depletion In some particular embodiments, the energy depletion comprises a condition substantially free of carbon sources, such as low glucose concentration and low pyruvate concentration, e.g., a substantially glucose-free and substantially pyruvate-free condition.

In some embodiments, the energy depletion is for at least about: 10, 20, 30, 40, 50, 60 minutes, e.g., at least about: 30, 40, 45, 50, 55, 60, 90, 120, 150, or 180 minutes or 1, 1.5, 2, 2.5, 3, 3.5, 4, 4.5, 5, 5.5, 6, 6.5, 7, 7.5, 8, 8.5, 9, 9.5, or 10 hours.

Energy depletion consonant with the invention potentiates the sperm. "Potentiate" or "potentiating" sperm means to condition sperm such that, upon a suitable induction, e.g., removing or reversing the energy depletion and, e.g., incubating the sperm in capacitation conditions or staged energy reintroduction, the sperm rapidly recover motility, such as one or more of: an increased proportion of hyperactivated, intermediate, or progressive motility sperm (or an increased proportion of a combination of two (such as hyperactivated and intermediate) or all three), and/or increased curvilinear velocities.

Staged Energy Reintroduction

Following energy depletion sufficient to potentiate the sperm, an effective amount of a first and then an effective amount of a second energy source is provided to the potentiated sperm. In some embodiments, the time between providing an effective amount of a first energy source after potentiating the sperm and providing an effective amount of a second energy source is at least about: 1, 2, 3, 4, 5, 10, 15, 20, 25, 30, 35, 40, 45, 50, 55, or 60 minutes, e.g., at least 5, 6, 7, 8, 9, 10, 11, 12, 13, 14, 15, 16, 17, 18, 19, or 20 minutes, e.g., at least between about: 5-15 minutes. In some embodiments, the time between providing an effective amount of a first energy source after potentiating the sperm and providing an effective amount of a second energy source is longer, such as at least 2, 3, 4, or 5 hours, or more.

In some embodiments, the gluconeogenesis substrate is pyruvate, e.g., at a concentration of about: 0.15-0.66 mM, e.g., about 0.20-0.50 mM, such as about 0.25-0.40 mM, or about 0.30 mM. The forgoing concentrations are exemplary effective amounts of a gluconeogenesis substrate, for example, when provided as either a first or second energy source in the methods provided by the invention. The skilled artisan will recognize other effective amounts of gluconeogenesis substrates by virtue of their ability to increase sperm function consonant with the teachings of the invention. In some embodiments, the first energy source is a gluconeogenesis substrate, such as pyruvate. In some embodiments, the second energy source is a gluconeogenesis substrate, such as pyruvate.

In some embodiments, the glycolytic energy source is glucose, e.g., at a concentration of about: 0.6 mM-10.0 mM, 1.0-7.0 mM, 2.5-7.0 mM, 3.5-6.5 mM or 5 mM, e.g., at least about 1, 2, 3, or 4 mM. The forgoing concentrations are exemplary effective amounts of a glycolytic energy source, for example, when provided as either a first or second energy source in the methods provided by the invention. The skilled artisan will recognize other effective amounts of glycolytic energy sources by virtue of their ability to increase sperm function consonant with the teachings of the invention. In some embodiments, the first energy source is a glycolytic energy source, such as glucose. In some embodiments the second energy source is a glycolytic energy source, such as glucose. In some embodiments, the first energy source is a glycolytic energy source, such as glucose, while the second energy source is a gluconeogenesis substrate, such as pyruvate.

An additional condition regulated in some embodiments of the methods provided by the invention is the osmolarity (mOsm) or osmolality (mOsm/kg). In some embodiments, the method is performed at an osmolarity (or osmolality) ranging from between about: 200-280 mOsm (mOsm/kg), e.g., between about: 220-260, 225-255, 230-250 mOsm (mOsm/kg) during energy depletion, optionally, wherein upon addition of the first or second energy source, the osmolarity (or osmolality) is increased to at least about: 270, 275, 280, 285, 290, or 295 mOsm (mOsm/kg).

In some embodiments of the methods provided by the invention, additional components are provided to the sperm. For example, other components upstream and downstream of glycolysis such as NADH, NAD+, citrate, AMP, ADP, or a combination thereof are added in combination with at least the first energy source or the second energy source.

Some embodiments of the methods provided by the invention include assessment of the sperm. For example, in some embodiments, the methods include one or more quantitative assessments of sperm motility, e.g., by CASA, and/or measuring sperm quality, such as DNA fragmentation (e.g., by TUNEL), lipid peroxidation, reactive oxygen species, or a combination thereof.

The methods provided by the invention achieve increased sperm function. In some embodiments, relative to a suitable control sperm. In some embodiments the suitable control is sperm in standard capacitation medium (C-HTF), without a starvation step, while in some embodiments, the suitable control is sperm in standard capacitation medium (C-HTF) following a three hour starvation—e.g., starvation and reintroduction of effective amounts of energy sources without staging reintroduction of the energy sources.

Mammalian Sperm

The methods disclosed herein comprise increasing one or more functions of a sperm. The present disclosure also relates to promoting fertilization. Preparations of sperm with increased function are also provided. As used herein, the sperm can be from a vertebrate, preferably a mammal. Accordingly, the sperm of the present disclosure can be a mammalian sperm.

Mammals include, without limitation, humans, primates, rodents, wild or domesticated animals, including feral animals, farm animals, sport animals, and pets. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The mammalian sperm can be from a non-human mammal including, an ungulate, such as an even-toed ungulate (e.g., pigs, peccaries, hippopotamuses, camels, llamas, chevrotains (mouse deer), deer, giraffes, pronghorn, antelopes, goat-antelopes (which include sheep, goats and others), or cattle) or an odd-toed ungulate (e.g., horse, tapirs, and rhinoceroses), a non-human primate (e.g., a monkey, chimpanzees, cynomologous monkeys, spider monkeys, and macaques, e.g., Rhesus.), a Canidae (e.g., a dog) or a cat. The mammalian sperm can be from a member of the Laurasiatheria superorder. The Laurasiatheria superorder can include a group of mammals as described in Waddell et al., Towards Resolving the Interordinal Relationships of Placental Mammals. Systematic Biology 48 (1): 1-5 (1999). The Members of the Laurasiatheria superorder can include Eulipotyphla (hedgehogs, shrews, and moles), Perissodactyla (rhinoceroses, horses, and tapirs), Carnivora (carnivores), Cetartiodactyla (artiodactyls and cetaceans), Chiroptera (bats), and Pholidota (pangolins). A member of Laurasiatheria superorder can be an ungulate, e.g., an odd-toed ungulate or even-toed ungulate. An ungulate can be a pig. The mammalian sperm can be from a member of Carnivora, such as a cat, or a dog. In some embodiments, the mammalian sperm is a human, non-human primate, porcine, bovine, equine, ovine, canine, feline, or murine sperm. In some embodiments, the mammalian sperm is a human sperm.

In some embodiments, the mammalian sperm is from a healthy male mammal. In some embodiments, the mammalian sperm is from a male suffering from sperm dysfunction, for example, low sperm count, reduced motility of sperm, and abnormal morphology of sperm. In some embodiments, the mammalian sperm can be from a subfertile male or an oligospermic male. The mammalian sperm can be from a male suffering from, for example, oligospermia, Teratozoospermia, Asthenozoospermia, or Oligoasthenoteratozoospermia. Oligospermia refers to a condition characterized by sperm concentration of <20 million/ml. Asthenozoospermia refers to a condition characterized by reduced sperm motility. Teratozoospermia refers to a condition characterized by presence of sperm with abnormal morphology. Oligoasthenoteratozoospermia refers to a condition that includes oligozoospermia (low number of sperm), asthenozoospermia (poor sperm movement), and teratozoospermia (abnormal sperm shape). In some embodiments, the sperm is obtained from a subfertile male or an oligospermic male, e.g., having a sperm count below about: 20, 19, 18, 18, 16, 15, 14, 13, 12, 11, 10, 9, 8, 7, 6, 5, 4, 3, 2 million sperm per milliliter, e.g., less than 15 million sperm per milliliter.

In some embodiments, the sperm are enriched (or isolated) from semen prior to energy depletion. Any method of sperm enrichment or isolation can be used consonant with the invention, including density gradient centrifugation, swim up, microfluidics, or a combination thereof.

Sperm may be used in the methods provided by the invention either fresh or from a preserved stock. For example, in some embodiments, prior to treatment, the sperm are recovered from cryogenic storage. In other embodiments, prior to treatment, the sperm are recovered from non-cryogenic storage.

Different quantities of sperm can be used in the methods provided by the invention, including fractions of a single ejaculate or a whole ejaculate. In some embodiments, the sperm are pooled from two or more ejaculates (e.g., 2, 3, 4, 5, 6, or more ejaculates).

Methods of Obtaining Sperm Sample

Various methods of collection of viable sperm are known. Such methods include, for example, masturbation into sterile containers, the gloved-hand method, use of an artificial vagina, and electro-ejaculation. Animal semen can be collected by using artificial vagina, electro-ejaculator, or by massaging the ampule of the animal by hand. It can also be directly collected from any section of the male reproductive tract including testicular sperm, and sperm obtained from caput, corpus or cauda epididymis using different methodologies such as puncture of the testis or epididymis using surgical procedures or removing the testis or epididymis and collecting the sperm in surrounding media. The sperm are preferably collected or quickly transferred into an insulated container to avoid a rapid temperature change from physiological temperatures (typically about 35° C. to about 39° C.). The ejaculate typically contains about 0.5 to 15 billion sperm per milliliter, depending upon the species and particular animal. The number may be reduced if obtained from a subfertile male or male suffering from sperm dysfunction.

The sperm may be freshly collected sample from a source animal (e.g., a mammal), or can be previously thawed or cryopreserved sample. At the time of collection, or subsequently, the collected sperm may be combined with any of a number of various buffers that are compatible with sperm, such as TCA, HEPES, PBS, or any of the other buffers disclosed in U.S. Patent Application Publication No. US 2005/0003472, the content of which is hereby incorporated herein by reference. For example, a bovine semen sample typically containing about 0.5 to about 10 billion sperm cells per milliliter may be collected directly from the source mammal into a vessel containing a buffer to form a sperm suspension. The sperm suspension may also contain a range of other additives to maintain sperm viability. Exemplary additives include protein sources, antibiotics, growth factors, and compositions that regulate oxidation/reduction reactions intracellularly and/or extracellularly. Examples of each of these additives are well known in the art, as demonstrated in the disclosure of, for example, U.S. application Ser. Nos. 60/557,407 and 11/092,313, the content of each of which is hereby incorporated herein by reference. Alternatively, the semen sample may be collected into an empty container and then subsequently contacted with a buffer within several minutes to hours after collection to form the sperm suspension. In some embodiments, the sperm cells can be collected directly into a container containing energy depletion medium (e.g., HTF medium devoid of glucose, pyruvate and lactate) for incubation under energy depletion. In some embodiments, the sperm cells can be collected in an empty container and subsequently incubated under energy depleting conditions.

In some embodiments, sperm collection comprises washing sperm cells prior to carrying out the methods disclosed herein. Generally, washing involves centrifuging a sample of semen or thawed sperm through a diluting wash media, which allows collection of a sperm-rich pellet. After a sperm wash process, or in place of it, a specific procedure for the isolation of the motile sperm from a sample can be done.

In some embodiments, the sperms are isolated from semen prior to use in methods disclosed herein. In some embodiments, sperm with increased function can be further enriched, (for example, enriching sperm with increased motility), from sperm prepared according to methods disclosed herein. Generally, sperm are isolated or enriched by allowing the motile sperm to swim away from the dead sperm, non motile sperm and debris (sperm swim-up), by centrifuging the sperm through a density gradient, or by passing the sperm through a column that binds the dead sperm and debris. Isolating (or enriching) the spermatozoa from semen is performed by a method selected from the wash and spin method, the sedimentation method, the direct swim-up method, the pellet and swim-up method, and the buoyant density gradient method. These methods are well known in the art. They are traditionally used in assisted reproduction techniques and described in detail in "A textbook of In vitro Fertilization and Assisted Reproduction, The Bourn Hall guide to clinical and laboratory practice, editor: Peter R. Brinsden, The Parthenon Publishing Group" (1999). In some embodiments, the sperm prepared by the methods disclosed herein can be further enriched for motile sperms by isolation procedures such as the sedimentation method, the direct swim-up method, the pellet and swim-up method, and the buoyant density gradient method.

The direct swim-up method implies self-selection of motile sperms, essentially comprising layering an aliquot of medium on top of a semen sample or a preparation of sperm disclosed herein and allowing it to stand at room temperature for a certain period of time. The motile sperm cells will migrate into the top layer (medium), from which they can be recovered. The method may also include centrifugation step(s). The advantage of "swim-up" selected spermatozoa is that the motile cells present in the sample are isolated and concentrated and that the proportion of morphologically normal sperm is increased.

The method may be varied and combined with further isolation/separation techniques, depending on the amount of motile cells in the sample. For example, the swim-up procedure may be performed through the layering of 1 ml of medium containing albumin on 1 ml of underlying seminal liquid in a test tube. After one hour of incubation at 37° C. in the air or in 5% CO2 the upper phase of the medium to which the spermatozoa with better motility characteristics have migrated is collected. This technique may also comprise or be combined with a centrifugation step, for example centrifugation on Percoll gradients. In typical applications, a sperm containing solution is layered over a gradient material, preferably Percoll at 30-90% mixed with 0.05% pectin, and then subjected to centrifugation to collect sperm enriched for improved function. The separated, isolated or enriched spermatozoa are then used in methods disclosed herein or may be cryopreserved before being further processed, for example. In case of the preparation of sperms prepared by methods herein, they can be used for IVF, ICSI or artificial insemination following enrichment steps or may be cryo-preserved for later use, for example. Accordingly for any of these isolation, or enrichment methods, the sample may be semen, partially purified sperm, purified sperm, or sperm with increased function prepared by methods herein. In some embodiments, the percentage of motile cells is increased by at least 10%, at least 20%, at least 50%, at least 75%, at least 80%, or about 100% after isolating or enriching the sperm using isolation methods, such as direct swim up, the pellet and swim-up method, and the buoyant density gradient method compared to untreated semen sample or unenriched sperm preparation.

In some embodiments, after isolation, enrichment and washing, the sperm pellet can be resuspended in a medium suitable for further processing, including preservation medium, HTF medium for culturing, medium for energy depleting conditions (e.g., HTF devoid of glucose, lactate and pyruvate). As it relates to sperm with increased function prepared by methods disclosed herein, the sperm preparation can be resuspended in preservation medium, HTF medium for culturing, medium for insemination, assays of fertilization potential as described herein, in vitro fertilization, freezing, intrauterine insemination, cervical cap insemination, and the like. The sperm may be added to medium or the medium can be added to the sperm. The medium can be balanced salt solution which may contain zwitterionic buffers, such as TES, HEPES, PIPES, or other buffers, such as sodium bicarbonate. In general, the medium for diluting sperm or culturing sperm, oocytes, embryos or embryonic stem cells is a balanced salt solution, such as M199, Synthetic Oviduct Fluid, PBS, BO, Test-yolk, Tyrode's, HBSS, Ham's F10, HTF, Menezo's B2, Menezo's B3, Ham's F12, DMEM, TALP, Earle's Buffered Salts, CZB, KSOM, BWW Medium, and emCare Media (PETS, Canton, Tex.). In some embodiments, TALP or HTF is used for sperm culture medium, and CZB is used for embryo culture medium. The sperm, or embryo of the present disclosure can be preserved in a cryogenic medium comprising a cryoprotectant.

Suitable Control Sperm

A suitable control sperm can be sperm incubated under control conditions, i.e., in a control buffer such as, human tubal fluid ("HTF") medium or modified HTF medium and not in energy depletion conditions. HTF comprises a sodium bicarbonate buffering system and may be utilized for uses requiring a carbon dioxide atmosphere during incubation. Modified HTF comprises a combined sodium bicarbonate and HEPES ([4-2(2-hydroxyethyl)-1-piperazineethanesulfonic acid]) buffer. Suitable examples of HTF medium or modified HTF medium include those that are commercially available from Irvine Scientific, Santa Ana, Calif. In some embodiments, the incubating in energy depletion conditions can be incubating the HTF medium from which glucose, lactate and pyruvate has been omitted. The sperm may be incubated for a period sufficient to provide a measurable change in the motility (or other characteristics) of the sperm; in specific embodiments of the method, incubation is from 1 minute to 24 hours, 15 minutes to 3 hours, 30 minutes to 1.5 hours, about 1 hour, or any subrange or subvalue thereof. In some embodiments, a suitable control sperm is sperm which is incubated in energy depletion conditions followed by treatment with a first energy source (e.g., selected from a gluconeogenesis substrate, or a glycolytic substrate) or a second energy source (e.g., selected from a gluconeogenesis substrate, or a glycolytic substrate but not same as first energy source) independently. In some embodiments, a suitable control sperm is sperm which is incubated in energy depletion conditions followed by treatment with a gluconeogenesis substrate, or a glycolytic substrate independently. In some embodiments, a suitable control is a sperm which is incubated in energy depletion conditions followed by treatment with a first energy source and a second energy source simultaneously. In some embodiments, a suitable control sperm is a sperm which is incubated in energy depletion conditions followed by treatment with a gluconeogenesis substrate and a glycolytic substrate simultaneously. In some embodiments, a suitable control sperm is an untreated sperm. It is understood that a suitable control sperm can be at least one sperm or a population of sperm, for example, a sperm preparation, or a sperm suspension.

Sperm Preparation

In some embodiments, the invention provides sperm preparations, such as preparations of activated (e.g., sperm having been starved following introduction of an effective amount of both the first and second energy sources, enriched for hyperactivated and intermediate sperm), partially activated sperm (sperm having been starved and contacted with an effective amount of only a first energy source), or potentiated sperm. These are collectively "sperm preparations provided by the invention" or "preparations provided by the invention." In some embodiments the invention provides preparations of hyperactivated sperm comprising at least 5% hyperactivated sperm, e.g., at least about: 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0%, or more hyperactivated sperm, e.g., between about: 5-20, 8.5-20, 10-20, or 12.5-20%. In some embodiments, the preparation also contains at least about: 5.5, 6.0, 6.5, 7.0, 7.5, 8.0, 8.5, 9.0, 9.5, 10.0, 12, 14, 15, 16, 18, 20, 22, 24, 25, 26, 28, or 30% intermediate motility sperm, e.g., between about 20.5-30%, 22.5-30%. Thus, in some embodiments, the percentage sum of hyperactivated and intermediate motility sperm is at least: 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 21.0, 21.5, 22.0, 22.5, 23.0, 23.5, 24.0, 24.5, 25, 26, 27, 28, 29, 30, 35, 40, 41, 42, 43, 44, 45, 46, 47, 48, 49, 50%, or more, e.g., between about: 10-50, 30.5-50, 32.5-50. As the skilled artisan will appreciate, sperm may be separated based on hyperactivation (and/or intermediate) phenotype, but in some embodiments, the foregoing percentages are based on preparations that have not been activated and then sorted based on hyperactivation (however, in some embodiments, sperm preparations may have been pre-processed, e.g., to separate or otherwise enrich sperm from other seminal components, including certain irregular sperm). In some embodiments, the hyperactivated (or intermediate motility, or hyperactivated and intermediate motility) sperm in the preparation have 10, 15, 20, 25, 30, 35, 40, 45, 50%, or more (e.g., 2, 3, 4, 5, 6, 7, 8, 9, 10-fold, or more) reduction in intracellular RNA concentration (such as small non-coding RNAs, including microRNA), relative to a suitable control. In some embodiments sperm in a preparation provided by the invention are characterized (as assessed by either bulk average metrics or percentages in categories) by altered sperm head morphology, increased tail movement (e.g., amplitude), or a combination thereof.

In some embodiments, the invention provides a preparation of sperm prepared by any one of the methods provided by the invention.

In some embodiments, the invention provides preparations of sperm prepared by enriching sperm from semen of a male subject, such as a normospermic male, sub fertile male, or oligospermic male, e.g., a subfertile (including oligospermic) male, incubating the sperm under energy depletion for a time suitable to potentiate the sperm and providing the sperm with a first energy source selected from: an effective amount of a glycolytic energy source or an effective amount of a gluconeogenesis substrate, but not an effective amount of both a glycolytic energy source and gluconeogenesis substrate.

For any of the preparations provided by the invention, sperm can be from any male subject, such as a mammal, and in some embodiments, a human. In some embodiments, the human is a normospermic male, or in other embodiments, the male is an oligospermic or subfertile (e.g., low sperm motility) subject.

Promoting Fertilization

The preparation of sperm with increased function prepared by the methods disclosed herein can be useful to promote fertilization. Accordingly, the present disclosure relates to a method of promoting fertilization. The method comprises incubating a sperm under energy depleting conditions to potentiate the sperm, providing the potentiated sperm with a first energy source and a second energy source in a serial manner to increase one or more sperm function, and providing the sperm with increased function with access to an egg under conditions to promote fertilization. The preparation of sperm with increased function can be applied in IVF, ICSI, artificial insemination (e.g., intra-uterine insemination) in human as well as in the biomedical research industry of animal models for human diseases (infertility, sperm dysfunction), and in the breeding and agricultural industries. The sperm with increased function prepared by the methods disclosed herein, can be provided access to an unfertilized egg of the same species as the sperm to promote in vitro fertilization, ICSI, or can be used for artificial insemination, including for example, intrauterine insemination of female subjects of the same species as the sperm.

In Vivo Fertilization

The sperm with increased function prepared by the methods disclose herein can be useful to promote fertilization in vivo by providing the sperm with increased function access to an egg in the reproductive tract of a female subject of the same species as the sperm. In vivo fertilization can be done by artificial insemination of sperm, for example, by intracervical insemination or intrauterine insemination. Standard artificial insemination and intrauterine insemination, and other methods are well known to those of skill in the art. In some embodiments, the sperm with increased function is provided access to an egg in the reproductive tract of a female subject by intrauterine insemination of the said sperm to promote fertilization of the egg. In other embodiments, the sperm can be provided the second energy source and access to an egg in vivo by intrauterine insemination of a mammalian sperm which has been incubated under energy depletion conditions and provided the first energy source in vitro. The sperm that is injected, may be used as held in suitable liquids. Liquid used for this purpose may be those liquids generally used as a medium for artificial insemination.

In Vitro Fertilization

The present methods and preparation of sperm disclosed herein is of particular benefit in promoting fertilization by assisted reproductive technology, e.g., embryo viability following ART, and in particular IVF. Other suitable ART techniques to which the present disclosure is applicable include, but are not limited to, gamete intrafallopian transfer (GIFT), zygote intrafallopian transfer (ZIFT), blastocyst transfer (BT), intracytoplasmic sperm injection (ICSI), gamete, embryo and cell cryopreservation, in vitro preparation of embryos for embryo biopsy and other forms of embryo micromanipulation including formation of embryos by nuclear transfer and production transgenic lines and genetically modified lines. It is also applicable to production of embryonic stem cell lines.

In some embodiments, the sperm with increased function prepared by the methods disclosed herein can be used to fertilize an egg in vitro, such as for example, by microinjection, including intracytoplasmic sperm injection (ICSI), and other methods well known to those in the art. Typically, in IVF, after fertilization, the cells are grown to the blastocyst stage and then implanted. The methods disclosed herein result in increase in formation of an embryo with longer viability and increased ability to develop into a 2-cell stage, blastocyst stage. Accordingly, the preparation of sperm disclosed herein can be useful in vitro fertilization procedures, including, for example ICSI.

The methods of the present disclosure encompass providing the sperm prepared by methods herein with access to an egg to promote in vitro fertilization. Providing the sperm access in vitro to the egg may be carried out in an appropriate medium. The medium used for this purpose can be a medium generally used as a medium for in vitro fertilization, for example, HTF medium. Temperature conditions for providing access may be a general temperature to be used in vitro fertilization, for example, can be an average body or a temperature close thereto of the mammal. Time for providing access may be any time that is generally required in vitro fertilization, but not particularly limited, and preferably from 6 to 24 hours. In vitro fertilization rate can be determined by incubating one or more sperms with matured oocytes for about 24 hr. Oocytes are then be stained with a 1% aceto-orcein stain to determine the percent fertilized, or left in culture to divide and the number of embryos formed are counted. Oocytes can be matured in vitro in M199 media with 50 μg luteinizing hormone/ml (Brackett and Zuelke, Theriogenology 39:43, 1993)

Fertilization Uses

These methods and preparation of sperm disclosed herein are generally applicable to many species, including human, bovine, canine, equine, porcine, ovine, avian, rodent and others. Although useful whenever fertilization is desired, the present methods have particular use in animals and humans that have a fertilization dysfunction in order to increase the likelihood of conception. Such dysfunctions include low sperm count, reduced motility of sperm, and abnormal morphology of sperm. Accordingly, the methods disclosed herein can be useful for preparation of sperm with increased function in infertility clinics prior to their use in vitro fertilization or intrauterine insemination. The methods described herein can be used to improve artificial insemination, IVF or ICSI in exotic species and/or endangered species. As such the methods can find use for promoting fertilization in animals maintained captive in a zoo, and in conservation programs aiming to improve reproduction in animals that are close to extinction in the wild. For example, the methods and preparation of sperm of the present disclosure can be used to improve fertilization and pregnancy rates in animal husbandry, for species of agricultural value, and in species bred for conservation purposes.

In addition, the methods and compositions of the present invention are useful in artificial insemination procedures, e.g., in commercial breedings. The method can be carried out with sperm from domesticated animals, especially livestock, as well as with sperm from wild animals (e.g., endangered species). For example, as disclosed herein, embodiments of the methods and compositions of the disclosure find application in bovine reproduction. The methods and preparation can be useful for artificial insemination in the livestock production industry where it is desirable to influence the outcome towards offspring having one or more preferred characteristics or traits by introducing specific genetically-determined traits into the livestock, e.g., offspring of a particular gender, offspring with enhanced milk production, offspring for quality meat production. Use of the methods described herein will result in improved pregnancy rates. Mammalian sperm are frequently damaged by freezing and thawing and results in lower fertility. By improving the performance of the viable sperm, sperm prepared by methods disclosed herein when used for insemination may promote a higher pregnancy rate per estrus cycle, reducing the number of cycles required to ensure conception and hence reducing the overall cost of artificial insemination.

Semen from animals with highly desirable traits could be used to inseminate more females because fewer cycles would be needed to ensure conception in any one female. For such applications, the semen is obtained from a male with desired characteristics. In order to influence gender outcome of the resulting offspring, the sperm preparation can be sorted into X- and Y chromosome bearing cells, and/or enriched for sperm with one or more increased sperm function disclosed herein. The sperm may be sorted by commonly used methods, for example, as described in Johnson et al. (U.S. Pat. No. 5,135,759) using a flow cytometer/cell sorter into X and Y chromosome-bearing sperm enriched populations. The sperm prepared by the methods disclosed herein can be sorted the into a population comprising a certain percent X chromosome bearing or Y chromosome bearing sperm cells. For example, the spermatozoa of one of the populations may comprise at least about 65% X chromosome bearing or Y chromosome bearing sperm cells, at least about 70% X chromosome bearing or Y chromosome bearing sperm cells, at least about 75% X chromosome bearing or Y chromosome bearing sperm cells, at least about 80% X chromosome bearing or Y chromosome bearing sperm cells, at least about 85% X chromosome bearing or Y chromosome bearing sperm cells, at least about 90% X chromosome bearing or Y chromosome bearing sperm cells, or even at least about 95% X chromosome bearing or Y chromosome bearing sperm cells. In some embodiments, the sorting can be done prior to preparing the sperm with increased function as disclosed herein. In some embodiments, the sorting can be done prior to providing the sperm with increased function with access to an egg for fertilization as in IVF, ICSI or AI.

The methods and preparations provided by the invention can be used in assisted fertilization, such as IVF, including by ICSI (intracytoplasmic sperm injection). In some embodiments, any of the methods provided by the invention can include the step of providing the sperm to a female reproductive tract, optionally wherein the effective amount of a second energy source is provided in the female reproductive tract. In some embodiments, a sperm preparation provided by the invention (having increased sperm function)

can be provided access to an egg for a time sufficient to fertilize the egg, which egg may be ex vivo (e.g., IVF, including ICSI) or, in some embodiments, in a female reproductive tract. Such methods, in some embodiments, entail a subsequent implantation of the fertilized egg in a female carrier.

In some embodiments, the invention provides methods of fertilization comprising providing a preparation provided by the invention that has not been contacted with an effective amount of a second energy source with access to an egg and an effective amount of a second energy source so as to provide an effective amount of both a gluconeogenesis substrate and a glycolytic energy source for a time sufficient to fertilize the egg. In some embodiments, these methods are performed in vitro. In other embodiments, these methods are performed in vivo, in the reproductive tract (vagina or uterus) of a female.

Articles of Manufacture

In some embodiments, the invention also provides articles of manufacture and kits, e.g., suitable for performing any of the methods provided by the invention or preparing any of the preparations provided by the invention. For example, in some embodiments, the invention provides articles of manufacture comprising a sperm potentiating solution that, upon contact with sperm, induces energy depletion; a first solution providing a first energy source selected from: an effective amount of a glycolytic energy source or an effective amount of a gluconeogenesis substrate, but not an effective amount of both a glycolytic energy source and gluconeogenesis substrate; and a second solution providing an effective amount of a second energy source. In some embodiments, the articles of manufacture further include a sperm isolating matrix. In more some embodiments, the sperm isolating matrix is silanized silica, optionally wherein the silanized silica is in media substantially free of any glycolytic energy source or gluconeogenesis substrate. In some embodiments, the kit comprises instructions for carrying out the methods disclosed herein. The kit can also include a washing medium, a preservation medium, culture medium (e.g., HTF), a diluent, and the like. The kits can further contain adjuvants, reagents, and buffers necessary.

The kits can also include a carrier, package, or container that is compartmentalized to receive one or more containers such as vials, tubes, and the like, each of the container(s) comprising one of the separate elements, such as the potentiating solution, first solution providing the first energy source, and second solution providing the second energy source to be used in a method described herein. Suitable containers include, for example, bottles, vials, syringes, and test tubes. The containers can be formed from a variety of materials such as glass or plastic. The articles of manufacture provided herein contain packaging materials. Examples of pharmaceutical packaging materials include, but are not limited to, blister packs, bottles, tubes, bags, containers, bottles, and any packaging material suitable for use in methods disclosed herein. A kit typically includes labels listing contents and/or instructions for use, and package inserts with instructions for use. A set of instructions can also be included.

EXAMPLES

The present disclosure will be described in greater detail by way of the following specific examples. The following examples are offered for illustrative purposes, and are not intended to limit the invention in any manner. Those of skill in the art will readily recognize a variety of non-critical parameters that can be changed or modified to yield alternative embodiments according to the invention. All patents, patent applications, and printed publications listed herein are incorporated herein by reference in their entirety.

Example 1: Materials and Methods

Media

Media for human sperm capacitation was Human Tubal Fluid (Complete HTF or C-HTF) medium, containing 97.8 mM NaCl, 4.7 mM KCl, 2 mM CaCl2, 0.37 mM KH2PO4, 0.2 mM MgSO4. 7H2O, 25.1 mM NaHCO3-, 0.33 mM Na-pyruvate, 2.78 mM glucose, lactate 21.4 mM and 5 mg/mL human serum albumin (HSA), 10 µg/mL gentamicin and phenol red 0.0006% at pH 7.4 equilibrated with 5% CO2. For sperm starvation treatment glucose, lactate and pyruvate were omitted from the HTF media above (F-HTF, test media).

Semen Samples

Semen samples were obtained from healthy males or males seeking treatment for infertility by masturbation into sterile containers. Ejaculates were liquified for up to 2 hours prior to processing for the experiment. Following liquefaction, the volume of the ejaculate was divided equally for processing into F-HTF (test) conditions or C-HTF (control conditions). Semen samples were processed by either density-gradient centrifugation or direct swim up method to collect viable sperm cells.

Sperm Processing

Density Gradient Centrifugation

Following liquefaction, the entire volume of each ejaculate was equally divided over two different gradient conditions. The test sample was prepared using a 45-90% Percoll (Sigma, P-1644)) gradient in phosphate buffered saline. The control sample was prepared using an Isolate gradient (Irvine Scientific, Santa Ana, Calif.; 99264) in human tubal fluid. Both samples were centrifuged for 20 min at 500×g. Following centrifugation, the supernatant was removed, and the pellet washed with 10 ml media. The test sample was washed in F-HTF and the control sample was washed in C-HTF.

Sperm Swim Up

Following liquefaction, the entire volume of each ejaculate was divided into a test sample and control sample, as previously described. The test sample was layered gently with 2.5 ml of F-HTF. The control sample was layered with C-HTF medium. Tubes were carefully inclined at a 45° angle and incubated for 1 h at 37° C., 5% CO2. The supernatant was carefully collected, and washed F-HTF and the control sample was washed in C-HTF.

Analysis of Sperm Motility

Sperm suspensions of test and control sperm (6 µl) were loaded into one pre-warmed chamber slide (depth, 20 µm) (Leja slide, Spectrum Technologies) and placed on a microscope stage at 37° C. Sperm motility was examined using the CEROS II computer-assisted semen analysis (CASA) system (Hamilton Thorne Research, Beverly, Mass.). One-second tracks were captured using the following settings: 60 frames per second, 60 frames acquired, minimum contrast=80, minimum size=3 pixels, default cell size=6 pixels, default cell intensity=160, slow cells counted as motile, low VAP cutoff=10 µm/s, low VSL cutoff=0 µm/s, minimum intensity gate=0.18, maximum intensity gate=1.21, minimum size gate=0.56 pixels, maximum size gate=2.63 pixels, minimum elongation gate=0 pixels, and maximum elongation gate=99 pixels. Raw data were sorted and analyzed using the CASAnova parameters (Goodson et al., 2018, supra). At least 20 microscopy fields corresponding to a minimum of 500 sperm were analyzed in each experiment.

Example 2: Experimental Results

This example shows that serial reintroduction of energy source after nutrient depletion increases sperm hyperactivation.

Figure 2:
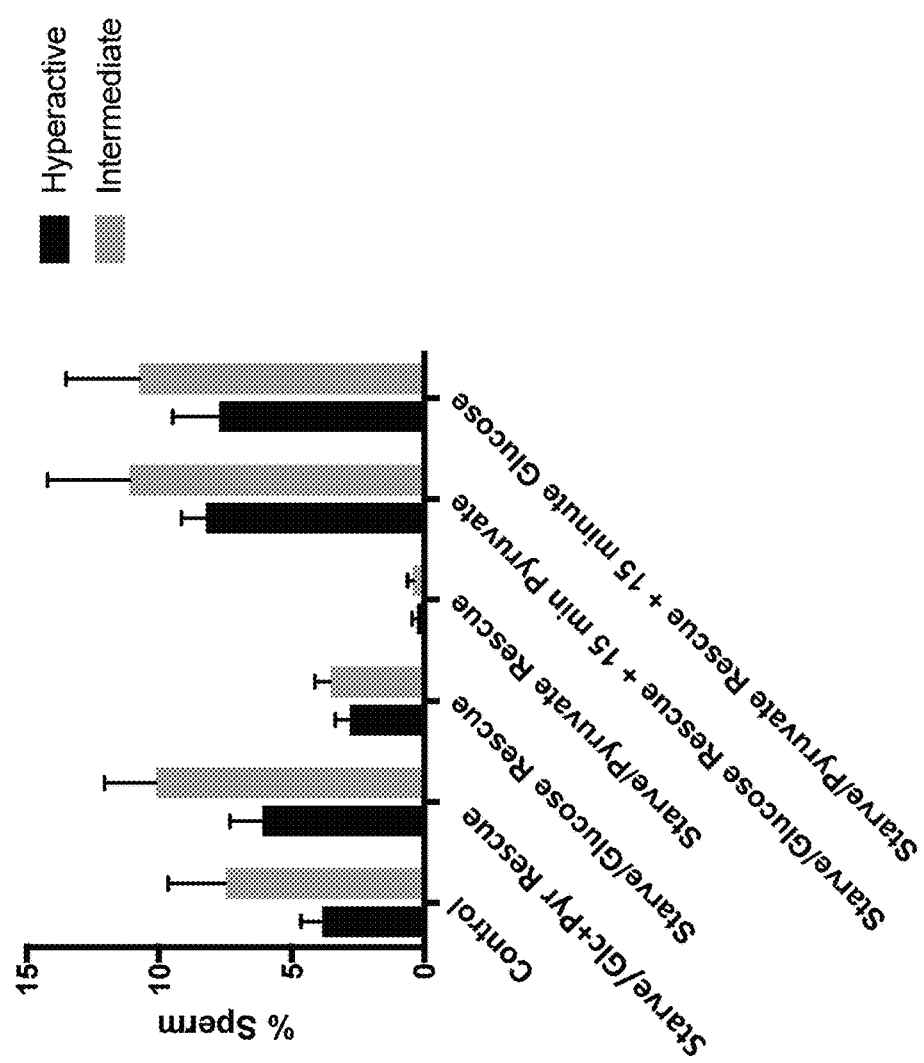
FIG. 2 is a bar graph of the percentage of hyperactive and intermediate motility sperm in control and starved (glucose, pyruvate, and lactate-free) conditions following: addition of glucose and pyruvate together (Starve/Rescue simultaneous), glucose only (Starve/Glucose rescue), pyruvate only (Starve/Pyruvate only), 1 hour glucose+15 minutes pyruvate (Starve/glucose rescue+15 minute pyruvate), or 1 hour pyruvate+15 minute Glucose.

Incubating sperm in a glucose, pyruvate and lactate-free media for three hours resulted in a reduction in motility as shown in FIG. 1. Rescue of sperm motility was tested with different energy substrates. When sperm were starved for 3 hour and rescued with a complete HTF sperm hyperactivation and intermediate motility were elevated compared with the control treatment (FIG. 2). In contrast, sperm treated with glucose (5 mM) or pyruvate (0.33 mM) alone did not improve sperm hyperactivation compared to the control (FIG. 2). Reintroduction of pyruvate alone had no impact on sperm motility from the starvation state, however, reintroduction of glucose alone restored motility to the levels of control (FIG. 2) suggesting that glucose is the major energy source required for sperm hyperactivation. Surprisingly, when pyruvate was added to the glucose-treated sperm or glucose to the pyruvate-treated sperm, this triggered a significant elevation in hyperactivation motility relative to control conditions or when both pyruvate and glucose were reintroduced to sperm at the same time Example 3: Enhancing Activation Osmolarity of C-HTF is approximately 290 mOsm, where F-HTF is approximately 243 mOsm. To illustrate that hypotonic conditions stress sperm such that when reversed, triggers elevated sperm motility and function, sperm are incubated in different conditions that are hypotonic, isotonic, or hypertonic in the presence of a carbon source that is not metabolized efficiently by the sperm such as trehalose, dextran, or other long chain sugar, and impacts on motility observed by CASA analysis during incubation in hypotonic conditions and following return to isotonic conditions. This includes adjusting concentrations of various ions such as calcium, sodium, and potassium during the potentiation phase, and evaluating motility following return to C-HTF. Additionally, impacts of increasing or decreasing the concentration of ions such as calcium, sodium and potassium during both the potentiation phase and the rescue phase are tested, as are the staged addition ions to mimic the ion cycling that occurs in the female reproductive tract during natural conception. In addition to motility, calcium ion flux is assessed. These manipulations, either alone or in conjunction with the described manipulation of glucose and pyruvate enhance the percentage of sperm that achieve hyperactive or intermediate motility.

Although human sperm exhibit reduced motility during the starvation phase of these treatments, the sperm do not completely stop moving suggesting that the cells are utilizing an internal energy source such as glycogen or degrading cellular components such as lipids, proteins, or RNA. Sperm exposed to the starvation phase are assessed for total lipid content, RNA content, and protein content. Proteomic, metabolomic, and lipidomic analysis are performed following the starvation phase, following addition of first energy source, and following addition of second energy source to illustrate intracellular changes associated with sperm motility states. Total RNA (including certain subfractions, such as mRNA or small non-coding RNA, such as microRNA) is measured in sperm treated with control conditions and sperm treated with test conditions, as illustrated in Example 2. The results of this analysis will indicate RNA is being used as an energy source by sperm.

Staging introduction of upstream carbon sources for glycolysis (such as glucose, mannose, fructose, dextrose, or sucrose) and downstream metabolites (such as pyruvate, lactate, succinate, citrate, fumarate, malate) change the rate of conversion of AMP to ATP resulting in improved sperm motility and function as compared to simultaneous addition. ATP and AMP levels are measured in sperm following starvation, introduction of first energy source and introduction of second energy source. Staged introduction of nutrients following starvation increases conversion of AMP to ATP.

Example 4

This example provides additional evidence that staged reintroduction of energy sources activates sperm.

Sperm samples from men seeking treatment for infertility were obtained from a fertility clinic. These samples included normally fertile and subfertile sperm. To improve sperm quality, samples were prepared by density gradient centrifugation as described in Example 1. Following liquefaction, the entire volume of each ejaculate was equally divided and subjected to two different density gradient conditions. The test sample was prepared using a 45-90% Percoll (Sigma, P-1644) gradient diluted in phosphate buffered saline solution devoid of nutrients with a final pH of 7.4 (F-PERCOLL). The control sample was prepared using a 45-90% Percoll gradient diluted in phosphate buffered saline solution with nutrients such as (lactate, glucose and pyruvate) with a final pH of 7.4 (C-PERCOLL). Both samples were centrifuged for 20 min at 500×g. Following centrifugation, the supernatant was removed, and the pellet washed with 10 ml media. The test sample was washed in F-HTF and the control sample was washed in C-HTF.

Samples were treated with C-HTF media as described in example 1 or separated by density gradient in a nutrient free media and washed with F-HTF. Sperm with F-HTF A) 1 hour incubation in F-HTF followed by addition of glucose (5 mM), pyruvate (0.33 mM) and lactate incubation for 1 hour 15 minutes, B) 1 hour incubation in F-HTF, addition of pyruvate for 1 hour, then addition of glucose for 15 minutes, or C) 1 hour incubation in F-HTF, addition of glucose for 1 hour then addition of pyruvate for 15 minutes. Samples were analyzed by CASA as outlined in Example 1. Results are shown in FIGS. 5A and 5B, and FIGS. 6A and 6B. Each test condition resulted in an increase in the number of sperm with intermediate and hyperactive motility relative to control, with the highest level of activation observed with treatments B and C.

Figure 3:
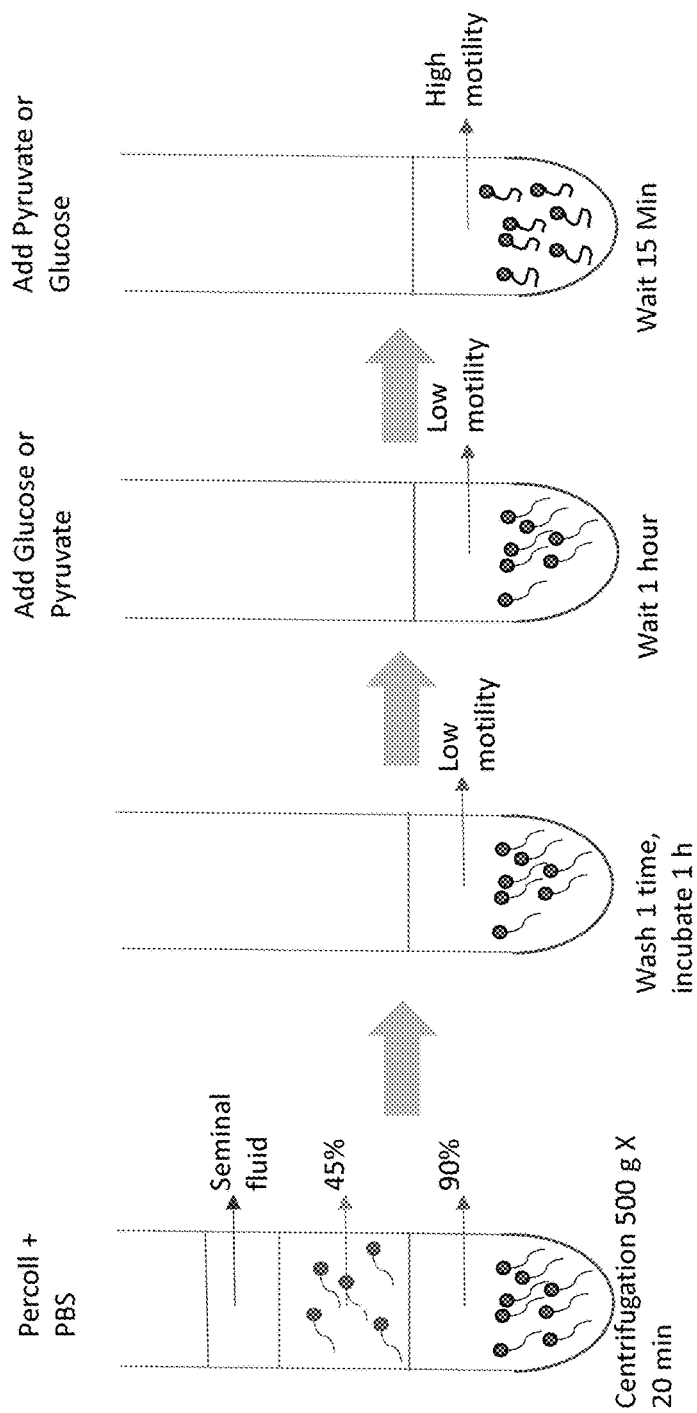
FIG. 3 is an illustration of density gradient isolation of sperm coupled to certain exemplary embodiments of methods provided by the invention.
Figure 4:
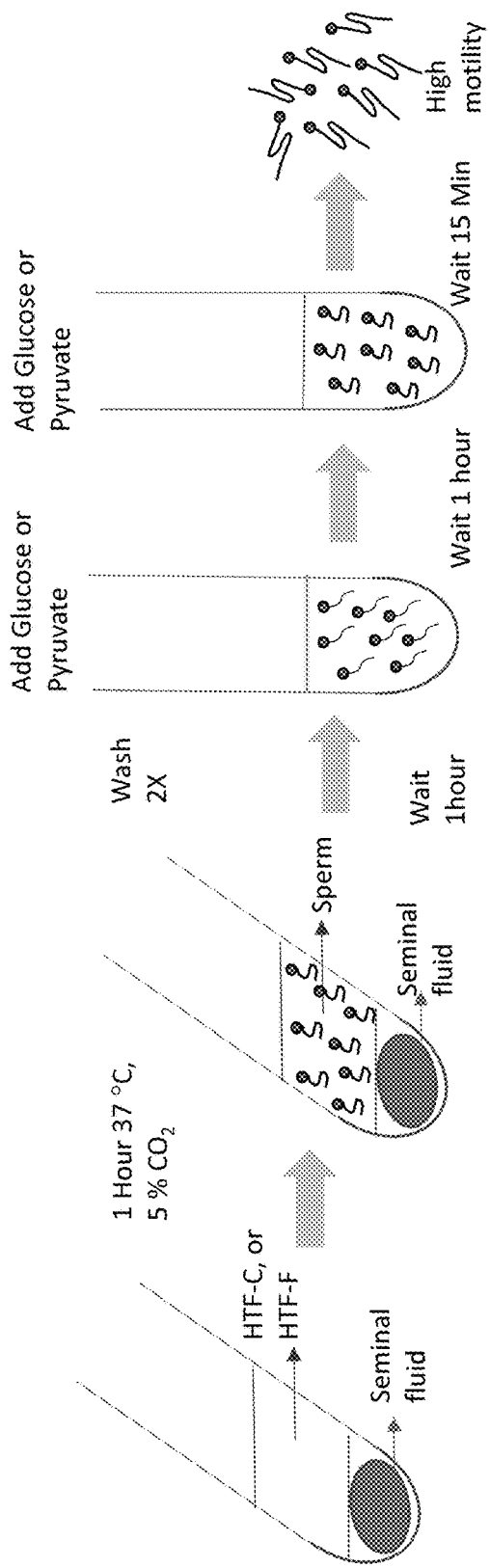
FIG. 4 is an illustration of swim-up isolation of sperm coupled to certain exemplary embodiments of methods provided by the invention.
Figure 5B:
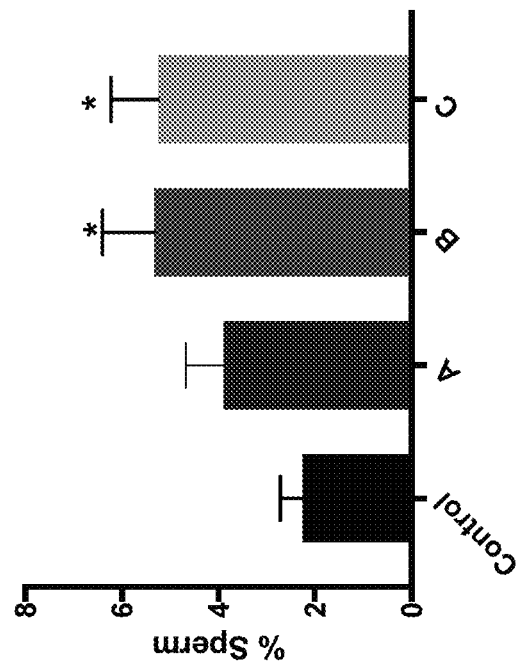
FIG. 5B is a bar graph of the percentage of hyperactive motility sperm+/−SEM in 7 different donors N=20, *: p<0.05 relative to control as determined by t-test. Semen samples were obtained from healthy volunteers.
Figure 5A:
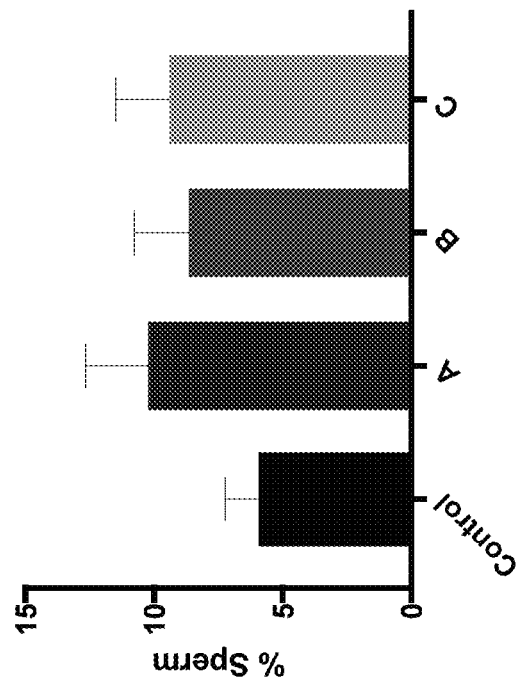
FIG. 5A is a bar graph of the percentage of intermediate motility sperm+/−SEM in 7 different donors N=20, *: $p<0.05$ relative to control as determined by t-test. Semen samples were obtained from healthy volunteers.
Figures 6A, 6B:
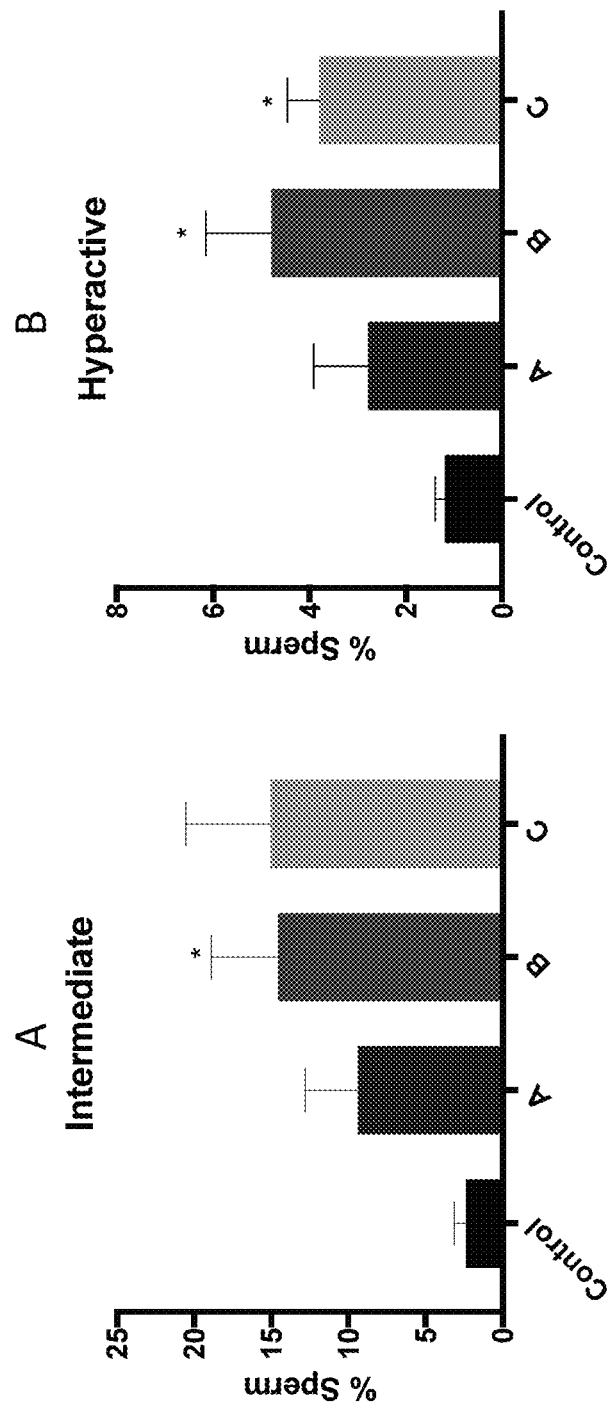
FIG. 6A is a bar graph of the percentage of intermediate motility sperm+/−SEM. N=5, *: p<0.05 relative to control as determined by t-test. Semen samples were obtained from men seeking treatment for infertility.
FIG. 6B is a bar graph of the percentage of hyperactive motility sperm+/−SEM. N=5, *: p<0.05 relative to control as determined by t-test. Semen samples were obtained from men seeking treatment for infertility.

To speed up the starvation state, sperm were separated by density gradient in a nutrient free media and washed with 10 ml F-HTF. After 1-hour incubation in F-HTF, sperm with reduced motility similar to the reduced motility as seen in FIG. 1 were primed with either pyruvate (0.33 mM) or glucose (5 mM) for one hour and then rescued with either (B) glucose (5 mM) or (C) pyruvate (0.33 mM) for 15 minutes as depicted in FIG. 3. Similar to the results shown in FIG. 2, this speed/starve protocol also significantly improved the sperm motility parameters shown in FIG. 5

Example 5

This example describes use of sperm treated according to certain embodiments of the invention to improve fertility in human subjects undergoing IUI.

Subjects are adult females (e.g., between 18 and 35 years old) without history of recurrent pregnancy loss and may or may not having previously attempted IUI. Subjects are treated with standard of care medicines (e.g., Clomid preparation, with Hcg triggering injection as indicated) and randomly assigned to receive either IUI of sperm prepared by diluting and centrifuging semen on C-HTF or F-HTF and collecting and resuspending cells in C-HTF or F-HTF. Alternatively, the sperm can be collected by density gradient centrifugation and washing and resuspending cells in C-HTF or F-HTF. Sperm are treated with F-HTF (e.g., for 1 hour), then either pyruvate or glucose is added and the sperm are incubated (e.g., for 1 hour), and then the sperm are used for inseminating the female. Sperm are treated with C-HTF (e.g., 2 hours), and then the sperm are used for inseminating the female. Pregnancies are monitored with regular follow-up. Females receiving sperm incubated in the absence of glucose (e.g., 5 mM) or pyruvate (e.g., 0.33 mM) followed by the staged addition of glucose or pyruvate are expected to exhibit a parameter of improved fertility, for example, increased rate of pregnancy, fetal heart rate (e.g., at 7 weeks), ongoing pregnancy (e.g., at 10 weeks) and/or live-birth rates.

Example 6

This example describes use of sperm treated according to certain embodiments of the invention to improve fertility in human subjects undergoing IVF.

Subjects are adult female subjects (e.g., between 18 and 35 years old) without history of recurrent pregnancy loss and may or may not having previously attempted IVF. Subjects are treated with standard of care medicines (e.g., ovulation suppression followed by ovulation stimulation, with Hcg triggering injection as indicated) prior to egg retrieval. Subjects are randomly assigned to the control group or the treatment group. In the control group, sperm are collected by density gradient centrifugation are resuspended in either sperm wash media, C-HTF or Fertilization media. Non-limiting examples of commercially available fertilization media include Global Total for fertilization (Origio), Continuous Single Culture®-NX Complete (Irvine), Sydney IVF Fertilization Medium (Cook Medical). In the treatment group, sperm are collected by density gradient centrifugation, are washed and resuspended in F-HTF for sufficient incubation to potentiate the sperm (e.g., 1 hour). Following this incubation, either pyruvate (0.33 mM) or glucose (5 mM) is added and the sperm are incubated (e.g., for 1 hour). Following this incubation, either glucose (5 mM) or pyruvate (0.33 mM) (whichever was not added in the first step) is added and the sperm are incubated (e.g., at least 15 minutes). For both the treatment and control groups, sperm will be incubated with eggs in vitro and fertilization rates and embryo development monitored. Embryos (e.g., at Day 5) will be transferred to the female and pregnancy will be determined by blood test (e.g., 2 weeks later). Pregnancies are monitored with regular follow-up. Females receiving embryos generated with sperm incubated in the absence of glucose and pyruvate followed by the staged addition of glucose and pyruvate are expected to exhibit an improved parameter of fertility, e.g., increased rates of fertilization, blastocyst development, pregnancy, fetal heart rate (e.g., at 7 weeks), ongoing pregnancy (e.g., at 10 weeks) and/or livebirth rates.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention (e.g., media, compositions, preparations, and methods) are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

What is claimed is:

1. A method for promoting fertilization comprising:
   (a) incubating a mammalian sperm under energy depletion conditions for a time suitable to potentiate the mammalian sperm;
   (b) providing the potentiated mammalian sperm from step (a) with an effective amount of a first energy source and a second energy source in a serial manner; and
   (c) providing the mammalian sperm resulting from step (b) with access to an egg under conditions to promote fertilization, wherein the effective amount is an amount sufficient to induce improved sperm function.

2. The method of claim 1, wherein one or more sperm function selected from curvilinear velocity, amplitude of lateral head displacement, autophagy, sperm capacitation, percentage of hyperactivated sperm, percentage of intermediate motility sperm and percentage of hyperactivated sperm and intermediate motility sperm, is improved relative to a method wherein the potentiated mammalian sperm are provided with only one of the first energy source and the second energy source or with the first energy source and the second energy source simultaneously.

3. The method of claim 1, wherein the first energy source is a glycolytic energy source and the second energy source is a gluconeogenesis substrate, or the first energy source is the gluconeogenesis substrate and the second energy source is the glycolytic energy source, further wherein the mammalian sperm of step (a) is a human sperm.

4. The method of claim 3, wherein the method is performed in vitro.

5. The method of claim 3, wherein step (c) is performed in vivo, in the reproductive tract of a female subject by artificial insemination in the vagina or intrauterine insemination (IUI) of the mammalian sperm from step (b).

6. The method of claim 1, wherein providing the second energy source of step (b) is performed in vivo, in the reproductive tract of a female subject by intrauterine insemination (IUI) of the potentiated mammalian sperm provided with an effective amount of the first energy source.

7. The method of claim 6, wherein the first energy source is a gluconeogenesis substrate that is pyruvate and the second energy source is a glycolytic energy source.

8. The method of claim 4, wherein step (c) comprises incubating the mammalian sperm from step (b) with the egg, or injecting the mammalian sperm from step (b) into the cytoplasm of the egg to promote in vitro fertilization of the egg.

9. The method of claim 1, wherein promoting fertilization comprises generation of an embryo, wherein the embryo exhibits increased viability and/or improved implantation relative to an embryo generated by a suitable control sperm.

10. The method of claim 1, wherein promoting fertilization comprises generation of an embryo which develops to at least a 2-cell developmental stage, a blastocyst developmental stage, or an offspring.

11. The method of claim 1, wherein the mammalian sperm of step (a) is from an oligospermic subject or a subfertile subject.

12. The method of claim 1, wherein the mammalian sperm of step (a) is a human, non-human primate, porcine, bovine, equine, ovine, canine, feline, or murine sperm.

13. The method of claim 12, wherein the mammalian sperm of step (a) is a human sperm.

14. The method of claim 1, wherein the mammalian sperm of step (a) is a sperm recovered from a non-cryogenic or cryogenic storage.

15. The method of claim 1, wherein the mammalian sperm of step (a) is provided as a pool of two or more ejaculates.

16. The method of claim 1, wherein the mammalian sperm of step (a) is enriched from semen prior to step (a) by density gradient centrifugation, swim up, or microfluidics.

17. The method of claim 1, wherein the method is performed at an osmolality ranging from 200-280 mOsm/kg.

18. The method of claim 1, wherein step (b) further comprises providing the mammalian sperm with one or more components upstream or downstream of glycolysis in combination with at least the first energy source or the second energy source.

19. The method of claim 3, wherein the first energy source is selected from: (i) glucose or (ii) pyruvate; and the second energy source is selected from: (i) glucose or (ii) pyruvate, and wherein the first and second energy source are different.

20. The method of claim 1, wherein the incubating under energy depletion conditions of step (a) is for at least 10 minutes.

* * * * *